(12) United States Patent
Moffitt

(10) Patent No.: US 9,592,389 B2
(45) Date of Patent: Mar. 14, 2017

(54) VISUALIZATION OF RELEVANT STIMULATION LEADWIRE ELECTRODES RELATIVE TO SELECTED STIMULATION INFORMATION

(71) Applicant: BOSTON SCIENTIFIC NEUROMODULATION CORPORATION, Valencia, CA (US)

(72) Inventor: Michael A. Moffitt, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 256 days.

(21) Appl. No.: 14/211,575

(22) Filed: Mar. 14, 2014

(65) Prior Publication Data

US 2014/0200633 A1     Jul. 17, 2014

Related U.S. Application Data

(63) Continuation-in-part of application No. 13/481,524, filed on May 25, 2012, and a continuation-in-part of
(Continued)

(51) Int. Cl.
*A61N 1/36*     (2006.01)
*A61B 19/00*     (2006.01)
*A61N 1/372*     (2006.01)

(52) U.S. Cl.
CPC .......... *A61N 1/36185* (2013.01); *A61B 34/10* (2016.02); *A61N 1/37235* (2013.01); *A61N 1/37247* (2013.01); *A61N 1/37241* (2013.01)

(58) Field of Classification Search
CPC   A61B 34/10; A61N 1/37247; A61N 1/37234; A61N 1/37241
See application file for complete search history.

(56) References Cited

U.S. PATENT DOCUMENTS 3,999,555 A    12/1976   Person
4,144,889 A    3/1979   Tyers et al.
(Continued)

FOREIGN PATENT DOCUMENTS

EP    1048320    11/2000
EP    1166819    1/2002
(Continued)

OTHER PUBLICATIONS

European Patent Office, International Search Report and the Written Opinion in International Application No. PCT/US2014/027782, mailed Jun. 25, 2014, 14 pages.
(Continued)

*Primary Examiner* — Mark W Bockelman
(74) *Attorney, Agent, or Firm* — Lowe Graham Jones PLLC; Bruce E. Black

(57) ABSTRACT

A system and method for graphically identifying candidate electrodes of a leadwire for stimulation of a patient anatomy includes a processor obtaining data corresponding to an anatomic region, identifying a spatial relationship between electrodes of the leadwire to the anatomic region, based on the identifying, selecting a subset of the electrodes of the leadwire, generating, based on the obtained data and the selected subset, a graphical output arrangement that includes a model of the leadwire including graphical representations of at least some of the electrodes and a graphical selection marking identifying the selected subset of the electrodes.

33 Claims, 6 Drawing Sheets

Related U.S. Application Data application No. 13/481,497, filed on May 25, 2012, and a continuation-in-part of application No. 14/011,817, filed on Aug. 28, 2013, and a continuation-in-part of application No. 14/011,836, filed on Aug. 28, 2013, and a continuation-in-part of application No. 14/011,870, filed on Aug. 28, 2013.

(60) Provisional application No. 61/793,773, filed on Mar. 15, 2013, provisional application No. 61/491,092, filed on May 27, 2011, provisional application No. 61/693,866, filed on Aug. 28, 2012, provisional application No. 61/699,115, filed on Sep. 10, 2012, provisional application No. 61/699,135, filed on Sep. 10, 2012, provisional application No. 61/753,232, filed on Jan. 16, 2013.

(56) References Cited

U.S. PATENT DOCUMENTS

| | | |
|---|---|---|
| 4,177,818 A | 12/1979 | De Pedro |
| 4,341,221 A | 7/1982 | Testerman |
| 4,378,797 A | 4/1983 | Osterholm |
| 4,445,500 A | 5/1984 | Osterholm |
| 4,735,208 A | 4/1988 | Wyler et al. |
| 4,765,341 A | 8/1988 | Mower et al. |
| 4,841,973 A | 6/1989 | Stecker |
| 5,067,495 A | 11/1991 | Brehm |
| 5,099,846 A | 3/1992 | Hardy |
| 5,222,494 A | 6/1993 | Baker, Jr. |
| 5,255,693 A | 10/1993 | Dutcher |
| 5,259,387 A | 11/1993 | dePinto |
| 5,304,206 A | 4/1994 | Baker, Jr. et al. |
| 5,344,438 A | 9/1994 | Testerman et al. |
| 5,361,763 A | 11/1994 | Kao et al. |
| 5,452,407 A | 9/1995 | Crook |
| 5,560,360 A | 10/1996 | Filler et al. |
| 5,565,949 A | 10/1996 | Kasha, Jr. |
| 5,593,427 A | 1/1997 | Gliner et al. |
| 5,601,612 A | 2/1997 | Gliner et al. |
| 5,607,454 A | 3/1997 | Cameron et al. |
| 5,620,470 A | 4/1997 | Gliner et al. |
| 5,651,767 A | 7/1997 | Schulmann |
| 5,711,316 A | 1/1998 | Elsberry et al. |
| 5,713,922 A | 2/1998 | King |
| 5,716,377 A | 2/1998 | Rise et al. |
| 5,724,985 A | 3/1998 | Snell et al. |
| 5,749,904 A | 5/1998 | Gliner et al. |
| 5,749,905 A | 5/1998 | Gliner et al. |
| 5,776,170 A | 7/1998 | MacDonald et al. |
| 5,782,762 A | 7/1998 | Vining |
| 5,843,148 A | 12/1998 | Gijsbers et al. |
| 5,859,922 A | 1/1999 | Hoffmann |
| 5,868,740 A | 2/1999 | LeVeen et al. |
| 5,897,583 A | 4/1999 | Meyer et al. |
| 5,910,804 A | 6/1999 | Fortenbery et al. |
| 5,925,070 A | 7/1999 | King et al. |
| 5,938,688 A | 8/1999 | Schiff |
| 5,938,690 A | 8/1999 | Law et al. |
| 5,978,713 A | 11/1999 | Prutchi et al. |
| 6,016,449 A | 1/2000 | Fischell et al. |
| 6,029,090 A | 2/2000 | Herbst |
| 6,029,091 A | 2/2000 | de la Rama et al. |
| 6,050,992 A | 4/2000 | Nichols |
| 6,058,331 A | 5/2000 | King |
| 6,066,163 A | 5/2000 | John |
| 6,083,162 A | 7/2000 | Vining |
| 6,094,598 A | 7/2000 | Elsberry et al. |
| 6,096,756 A | 8/2000 | Crain et al. |
| 6,106,460 A | 8/2000 | Panescu et al. |
| 6,109,269 A | 8/2000 | Rise et al. |
| 6,128,538 A | 10/2000 | Fischell et al. |
| 6,129,685 A | 10/2000 | Howard, III |
| 6,146,390 A | 11/2000 | Heilbrun et al. |
| 6,161,044 A | 12/2000 | Silverstone |
| 6,167,311 A | 12/2000 | Rezai |
| 6,181,969 B1 | 1/2001 | Gord |
| 6,192,266 B1 | 2/2001 | Dupree et al. |
| 6,205,361 B1 | 3/2001 | Kuzma |
| 6,208,881 B1 | 3/2001 | Champeau |
| 6,240,308 B1 | 5/2001 | Hardy et al. |
| 6,246,912 B1 | 6/2001 | Sluijter et al. |
| 6,253,109 B1 | 6/2001 | Gielen |
| 6,289,239 B1 | 9/2001 | Panescu et al. |
| 6,301,492 B1 | 10/2001 | Zonenshayn |
| 6,310,619 B1 | 10/2001 | Rice |
| 6,319,241 B1 | 11/2001 | King et al. |
| 6,336,899 B1 | 1/2002 | Yamazaki |
| 6,343,226 B1 | 1/2002 | Sunde et al. |
| 6,351,675 B1 | 2/2002 | Tholen et al. |
| 6,353,762 B1 | 3/2002 | Baudino et al. |
| 6,366,813 B1 | 4/2002 | Dilorenzo |
| 6,368,331 B1 | 4/2002 | Front et al. |
| 6,389,311 B1 | 5/2002 | Whayne et al. |
| 6,393,325 B1 | 5/2002 | Mann et al. |
| 6,421,566 B1 | 7/2002 | Holsheimer |
| 6,435,878 B1 | 8/2002 | Reynolds et al. |
| 6,442,432 B2 | 8/2002 | Lee |
| 6,463,328 B1 | 10/2002 | John |
| 6,491,699 B1 | 12/2002 | Henderson et al. |
| 6,494,831 B1 | 12/2002 | Koritzinsky |
| 6,507,759 B1 | 1/2003 | Prutchi et al. |
| 6,510,347 B2 | 1/2003 | Borkan |
| 6,516,227 B1 | 2/2003 | Meadows et al. |
| 6,517,480 B1 | 2/2003 | Krass |
| 6,539,263 B1 | 3/2003 | Schiff et al. |
| 6,560,490 B2 | 5/2003 | Grill et al. |
| 6,579,280 B1 | 6/2003 | Kovach et al. |
| 6,600,956 B2 | 7/2003 | Maschino et al. |
| 6,606,523 B1 | 8/2003 | Jenkins |
| 6,609,029 B1 | 8/2003 | Mann et al. |
| 6,609,031 B1 | 8/2003 | Law et al. |
| 6,609,032 B1 | 8/2003 | Woods et al. |
| 6,622,048 B1 | 9/2003 | Mann et al. |
| 6,631,297 B1 | 10/2003 | Mo |
| 6,654,642 B2 | 11/2003 | North et al. |
| 6,662,053 B2 | 12/2003 | Borkan |
| 6,675,046 B2 | 1/2004 | Holsheimer |
| 6,684,106 B2 | 1/2004 | Herbst |
| 6,687,392 B1 | 2/2004 | Touzawa et al. |
| 6,690,972 B2 | 2/2004 | Conley et al. |
| 6,690,974 B2 | 2/2004 | Archer et al. |
| 6,692,315 B1 | 2/2004 | Soumillion et al. |
| 6,694,162 B2 | 2/2004 | Hartlep |
| 6,694,163 B1 | 2/2004 | Vining |
| 6,708,096 B1 | 3/2004 | Frei et al. |
| 6,741,892 B1 | 5/2004 | Meadows et al. |
| 6,748,098 B1 | 6/2004 | Rosenfeld |
| 6,748,276 B1 | 6/2004 | Daignault, Jr. et al. |
| 6,778,846 B1 | 8/2004 | Martinez et al. |
| 6,788,969 B2 | 9/2004 | Dupree et al. |
| 6,795,737 B2 | 9/2004 | Gielen et al. |
| 6,827,681 B2 | 12/2004 | Tanner et al. |
| 6,830,544 B2 | 12/2004 | Tanner |
| 6,845,267 B2 | 1/2005 | Harrison et al. |
| 6,850,802 B2 | 2/2005 | Holsheimer |
| 6,895,280 B2 | 5/2005 | Meadows et al. |
| 6,909,913 B2 | 6/2005 | Vining |
| 6,937,891 B2 | 8/2005 | Leinders et al. |
| 6,937,903 B2 | 8/2005 | Schuler et al. |
| 6,944,497 B2 | 9/2005 | Stypulkowski |
| 6,944,501 B1 | 9/2005 | Pless |
| 6,950,707 B2 | 9/2005 | Whitehurst |
| 6,969,388 B2 | 11/2005 | Goldman et al. |
| 7,003,349 B1 | 2/2006 | Andersson et al. |
| 7,003,352 B1 | 2/2006 | Whitehurst |
| 7,008,370 B2 | 3/2006 | Tanner et al. |
| 7,008,413 B2 | 3/2006 | Kovach et al. |
| 7,035,690 B2 | 4/2006 | Goetz |
| 7,043,293 B1 | 5/2006 | Baura |
| 7,047,082 B1 | 5/2006 | Schrom et al. |
| 7,047,084 B2 | 5/2006 | Erickson et al. |
| 7,050,857 B2 | 5/2006 | Samuelsson et al. |

(56) References Cited

U.S. PATENT DOCUMENTS

| | | |
|---|---|---|
| 7,054,692 B1 | 5/2006 | Whitehurst et al. |
| 7,058,446 B2 | 6/2006 | Schuler et al. |
| 7,082,333 B1 | 7/2006 | Bauhahn et al. |
| 7,107,102 B2 | 9/2006 | Daignault, Jr. et al. |
| 7,127,297 B2 | 10/2006 | Law et al. |
| 7,136,518 B2 | 11/2006 | Griffin et al. |
| 7,136,695 B2 | 11/2006 | Pless et al. |
| 7,142,923 B2 | 11/2006 | North et al. |
| 7,146,219 B2 | 12/2006 | Sieracki et al. |
| 7,146,223 B1 | 12/2006 | King |
| 7,151,961 B1 | 12/2006 | Whitehurst et al. |
| 7,155,279 B2 | 12/2006 | Whitehurst et al. |
| 7,167,760 B2 | 1/2007 | Dawant et al. |
| 7,177,674 B2 | 2/2007 | Echauz et al. |
| 7,181,286 B2 | 2/2007 | Sieracki et al. |
| 7,184,837 B2 | 2/2007 | Goetz |
| 7,191,014 B2 | 3/2007 | Kobayashi et al. |
| 7,209,787 B2 | 4/2007 | DiLorenzo |
| 7,211,050 B1 | 5/2007 | Caplygin |
| 7,216,000 B2 | 5/2007 | Sieracki et al. |
| 7,217,276 B2 | 5/2007 | Henderson et al. |
| 7,218,968 B2 | 5/2007 | Condie et al. |
| 7,228,179 B2 | 6/2007 | Campen et al. |
| 7,231,254 B2 | 6/2007 | DiLorenzo |
| 7,236,830 B2 | 6/2007 | Gliner |
| 7,239,910 B2 | 7/2007 | Tanner |
| 7,239,916 B2 | 7/2007 | Thompson et al. |
| 7,239,926 B2 | 7/2007 | Goetz |
| 7,242,984 B2 | 7/2007 | DiLorenzo |
| 7,244,150 B1 | 7/2007 | Brase et al. |
| 7,252,090 B2 | 8/2007 | Goetz |
| 7,254,445 B2 | 8/2007 | Law et al. |
| 7,254,446 B1 | 8/2007 | Erickson et al. |
| 7,257,447 B2 | 8/2007 | Cates et al. |
| 7,266,412 B2 | 9/2007 | Stypulkowski |
| 7,294,107 B2 | 11/2007 | Simon et al. |
| 7,295,876 B1 | 11/2007 | Erickson |
| 7,299,096 B2 | 11/2007 | Balzer et al. |
| 7,308,302 B1 | 12/2007 | Schuler et al. |
| 7,313,430 B2 | 12/2007 | Urquhart et al. |
| 7,324,851 B1 | 1/2008 | DiLorenzo |
| 7,346,382 B2 | 3/2008 | McIntyre et al. |
| 7,388,974 B2 | 6/2008 | Yanagita |
| 7,437,193 B2 | 10/2008 | Parramon et al. |
| 7,463,928 B2 | 12/2008 | Lee et al. |
| 7,499,048 B2 | 3/2009 | Sieracki et al. |
| 7,505,815 B2 | 3/2009 | Lee et al. |
| 7,548,786 B2 | 6/2009 | Lee et al. |
| 7,565,199 B2 | 7/2009 | Sheffield et al. |
| 7,603,177 B2 | 10/2009 | Sieracki et al. |
| 7,617,002 B2 | 11/2009 | Goetz |
| 7,623,918 B2 | 11/2009 | Goetz |
| 7,650,184 B2 | 1/2010 | Walter |
| 7,657,319 B2 | 2/2010 | Goetz et al. |
| 7,672,734 B2 | 3/2010 | Anderson et al. |
| 7,676,273 B2 | 3/2010 | Goetz et al. |
| 7,680,526 B2 | 3/2010 | McIntyre et al. |
| 7,734,340 B2 | 6/2010 | De Ridder |
| 7,761,165 B1 | 7/2010 | He et al. |
| 7,826,902 B2 | 11/2010 | Stone et al. |
| 7,848,802 B2 | 12/2010 | Goetz et al. |
| 7,860,548 B2 | 12/2010 | McIntyre et al. |
| 7,904,134 B2 | 3/2011 | McIntyre et al. |
| 7,945,105 B1 | 5/2011 | Jaenisch |
| 7,949,395 B2 | 5/2011 | Kuzma |
| 7,974,706 B2 | 7/2011 | Moffitt et al. |
| 8,019,439 B2 | 9/2011 | Kuzma et al. |
| 8,175,710 B2 | 5/2012 | He |
| 8,180,601 B2 | 5/2012 | Butson et al. |
| 8,195,300 B2 | 6/2012 | Gliner et al. |
| 8,224,450 B2 | 7/2012 | Brase |
| 8,257,684 B2 | 9/2012 | Covalin et al. |
| 8,262,714 B2 | 9/2012 | Hulvershorn et al. |
| 8,364,278 B2 | 1/2013 | Pianca et al. |
| 8,429,174 B2 | 4/2013 | Ramani et al. |
| 8,452,415 B2 | 5/2013 | Goetz et al. |
| 8,543,189 B2 | 9/2013 | Paitel et al. |
| 8,606,360 B2 | 12/2013 | Butson et al. |
| 8,620,452 B2 | 12/2013 | King et al. |
| 8,918,184 B1 | 12/2014 | Torgerson et al. |
| 2001/0031071 A1 | 10/2001 | Nichols et al. |
| 2002/0032375 A1 | 3/2002 | Bauch et al. |
| 2002/0062143 A1 | 5/2002 | Baudino et al. |
| 2002/0087201 A1 | 7/2002 | Firlik et al. |
| 2002/0099295 A1 | 7/2002 | Gil et al. |
| 2002/0115603 A1 | 8/2002 | Whitehouse |
| 2002/0116030 A1 | 8/2002 | Rezai |
| 2002/0123780 A1 | 9/2002 | Grill et al. |
| 2002/0128694 A1 | 9/2002 | Holsheimer |
| 2002/0151939 A1 | 10/2002 | Rezai |
| 2002/0183607 A1 | 12/2002 | Bauch et al. |
| 2002/0183740 A1 | 12/2002 | Edwards et al. |
| 2002/0183817 A1 | 12/2002 | Van Venrooij et al. |
| 2003/0097159 A1 | 5/2003 | Schiff et al. |
| 2003/0149450 A1 | 8/2003 | Mayberg |
| 2003/0171791 A1 | 9/2003 | KenKnight et al. |
| 2003/0212439 A1 | 11/2003 | Schuler et al. |
| 2004/0034394 A1 | 2/2004 | Woods et al. |
| 2004/0044279 A1 | 3/2004 | Lewin et al. |
| 2004/0044378 A1 | 3/2004 | Holsheimer |
| 2004/0044379 A1 | 3/2004 | Holsheimer |
| 2004/0054297 A1 | 3/2004 | Wingeier et al. |
| 2004/0059395 A1 | 3/2004 | North et al. |
| 2004/0106916 A1 | 6/2004 | Quaid et al. |
| 2004/0133248 A1 | 7/2004 | Frei et al. |
| 2004/0152957 A1 | 8/2004 | Stivoric et al. |
| 2004/0181262 A1 | 9/2004 | Bauhahn |
| 2004/0186532 A1 | 9/2004 | Tadlock |
| 2004/0199216 A1 | 10/2004 | Lee et al. |
| 2004/0267330 A1 | 12/2004 | Lee et al. |
| 2005/0021090 A1 | 1/2005 | Schuler et al. |
| 2005/0033380 A1 | 2/2005 | Tanner et al. |
| 2005/0049649 A1 | 3/2005 | Luders et al. |
| 2005/0060001 A1 | 3/2005 | Singhal et al. |
| 2005/0060009 A1 | 3/2005 | Goetz |
| 2005/0070781 A1 | 3/2005 | Dawant et al. |
| 2005/0075689 A1 | 4/2005 | Toy et al. |
| 2005/0085714 A1 | 4/2005 | Foley et al. |
| 2005/0165294 A1 | 7/2005 | Weiss |
| 2005/0171587 A1 | 8/2005 | Daglow et al. |
| 2005/0228250 A1 | 10/2005 | Bitter et al. |
| 2005/0251061 A1 | 11/2005 | Schuler et al. |
| 2005/0261061 A1 | 11/2005 | Nguyen et al. |
| 2005/0261601 A1 | 11/2005 | Schuler et al. |
| 2005/0261747 A1 | 11/2005 | Schuler et al. |
| 2005/0267347 A1 | 12/2005 | Oster |
| 2005/0288732 A1 | 12/2005 | Schuler et al. |
| 2006/0004422 A1 | 1/2006 | De Ridder |
| 2006/0017749 A1 | 1/2006 | McIntyre et al. |
| 2006/0020292 A1 | 1/2006 | Goetz et al. |
| 2006/0069415 A1 | 3/2006 | Cameron et al. |
| 2006/0094951 A1 | 5/2006 | Dean et al. |
| 2006/0095088 A1 | 5/2006 | De Riddler |
| 2006/0155340 A1 | 7/2006 | Schuler et al. |
| 2006/0206169 A1 | 9/2006 | Schuler |
| 2006/0218007 A1 | 9/2006 | Bjorner et al. |
| 2006/0224189 A1 | 10/2006 | Schuler et al. |
| 2006/0235472 A1 | 10/2006 | Goetz et al. |
| 2006/0259079 A1 | 11/2006 | King |
| 2006/0259099 A1 | 11/2006 | Goetz et al. |
| 2007/0000372 A1 | 1/2007 | Rezai et al. |
| 2007/0017749 A1 | 1/2007 | Dold et al. |
| 2007/0027514 A1 | 2/2007 | Gerber |
| 2007/0043268 A1 | 2/2007 | Russell |
| 2007/0049817 A1 | 3/2007 | Preiss et al. |
| 2007/0067003 A1 | 3/2007 | Sanchez et al. |
| 2007/0078498 A1 | 4/2007 | Rezai et al. |
| 2007/0083104 A1 | 4/2007 | Butson et al. |
| 2007/0123953 A1 | 5/2007 | Lee et al. |
| 2007/0129769 A1 | 6/2007 | Bourget et al. |
| 2007/0135855 A1 | 6/2007 | Foshee et al. |
| 2007/0150036 A1 | 6/2007 | Anderson |
| 2007/0156186 A1 | 7/2007 | Lee et al. |
| 2007/0162086 A1 | 7/2007 | DiLorenzo |

(56) References Cited

U.S. PATENT DOCUMENTS

| | | |
|---|---|---|
| 2007/0162235 A1 | 7/2007 | Zhan et al. |
| 2007/0168004 A1 | 7/2007 | Walter |
| 2007/0168007 A1 | 7/2007 | Kuzma et al. |
| 2007/0185544 A1 | 8/2007 | Dawant et al. |
| 2007/0191887 A1 | 8/2007 | Schuler et al. |
| 2007/0191912 A1 | 8/2007 | Fischer et al. |
| 2007/0197891 A1 | 8/2007 | Shachar et al. |
| 2007/0203450 A1 | 8/2007 | Berry |
| 2007/0203532 A1 | 8/2007 | Tass et al. |
| 2007/0203537 A1 | 8/2007 | Goetz et al. |
| 2007/0203538 A1 | 8/2007 | Stone et al. |
| 2007/0203539 A1 | 8/2007 | Stone et al. |
| 2007/0203540 A1 | 8/2007 | Goetz et al. |
| 2007/0203541 A1 | 8/2007 | Goetz et al. |
| 2007/0203543 A1 | 8/2007 | Stone et al. |
| 2007/0203544 A1 | 8/2007 | Goetz et al. |
| 2007/0203545 A1 | 8/2007 | Stone et al. |
| 2007/0203546 A1 | 8/2007 | Stone et al. |
| 2007/0213789 A1 | 9/2007 | Nolan et al. |
| 2007/0213790 A1 | 9/2007 | Nolan et al. |
| 2007/0244519 A1 | 10/2007 | Keacher et al. |
| 2007/0245318 A1 | 10/2007 | Goetz et al. |
| 2007/0255321 A1 | 11/2007 | Gerber et al. |
| 2007/0255322 A1 | 11/2007 | Gerber et al. |
| 2007/0265664 A1 | 11/2007 | Gerber et al. |
| 2007/0276441 A1 | 11/2007 | Goetz |
| 2007/0282189 A1 | 12/2007 | Dan et al. |
| 2007/0288064 A1 | 12/2007 | Butson et al. |
| 2008/0027514 A1 | 1/2008 | DeMulling et al. |
| 2008/0039895 A1 | 2/2008 | Fowler et al. |
| 2008/0071150 A1 | 3/2008 | Miesel et al. |
| 2008/0081982 A1 | 4/2008 | Simon et al. |
| 2008/0086451 A1 | 4/2008 | Torres et al. |
| 2008/0103533 A1 | 5/2008 | Patel et al. |
| 2008/0114233 A1 | 5/2008 | McIntyre et al. |
| 2008/0114579 A1 | 5/2008 | McIntyre et al. |
| 2008/0123922 A1 | 5/2008 | Gielen et al. |
| 2008/0123923 A1 | 5/2008 | Gielen et al. |
| 2008/0133141 A1 | 6/2008 | Frost |
| 2008/0141217 A1 | 6/2008 | Goetz et al. |
| 2008/0154340 A1 | 6/2008 | Goetz et al. |
| 2008/0154341 A1 | 6/2008 | McIntyre et al. |
| 2008/0163097 A1 | 7/2008 | Goetz et al. |
| 2008/0183256 A1 | 7/2008 | Keacher |
| 2008/0188734 A1 | 8/2008 | Suryanarayanan et al. |
| 2008/0215118 A1 | 9/2008 | Goetz et al. |
| 2008/0227139 A1 | 9/2008 | Deisseroth et al. |
| 2008/0242950 A1 | 10/2008 | Jung et al. |
| 2008/0261165 A1 | 10/2008 | Steingart et al. |
| 2008/0269588 A1 | 10/2008 | Csavoy et al. |
| 2008/0300654 A1 | 12/2008 | Lambert et al. |
| 2008/0300797 A1 | 12/2008 | Tabibiazar et al. |
| 2009/0016491 A1 | 1/2009 | Li |
| 2009/0054950 A1 | 2/2009 | Stephens |
| 2009/0082640 A1 | 3/2009 | Kovach et al. |
| 2009/0082829 A1 | 3/2009 | Panken et al. |
| 2009/0112289 A1 | 4/2009 | Lee et al. |
| 2009/0118635 A1 | 5/2009 | Lujan et al. |
| 2009/0118786 A1 | 5/2009 | Meadows et al. |
| 2009/0149917 A1 | 6/2009 | Whitehurst et al. |
| 2009/0196471 A1 | 8/2009 | Goetz et al. |
| 2009/0196472 A1 | 8/2009 | Goetz et al. |
| 2009/0198306 A1 | 8/2009 | Goetz et al. |
| 2009/0198354 A1 | 8/2009 | Wilson |
| 2009/0204192 A1 | 8/2009 | Carlton et al. |
| 2009/0208073 A1 | 8/2009 | McIntyre et al. |
| 2009/0210208 A1 | 8/2009 | McIntyre et al. |
| 2009/0242399 A1 | 10/2009 | Kamath et al. |
| 2009/0276008 A1 | 11/2009 | Lee et al. |
| 2009/0281595 A1 | 11/2009 | King et al. |
| 2009/0281596 A1 | 11/2009 | King et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |
| 2010/0010566 A1 | 1/2010 | Thacker et al. |
| 2010/0010646 A1 | 1/2010 | Drew et al. |
| 2010/0023103 A1 | 1/2010 | Elborno |
| 2010/0023130 A1 | 1/2010 | Henry et al. |
| 2010/0030312 A1 | 2/2010 | Shen |
| 2010/0049276 A1 | 2/2010 | Blum et al. |
| 2010/0049280 A1 | 2/2010 | Goetz |
| 2010/0064249 A1 | 3/2010 | Groetken |
| 2010/0113959 A1 | 5/2010 | Pascual-Leone et al. |
| 2010/0121409 A1 | 5/2010 | Kothandaraman et al. |
| 2010/0135553 A1 | 6/2010 | Joglekar |
| 2010/0137944 A1 | 6/2010 | Zhu |
| 2010/0152604 A1 | 6/2010 | Kuala et al. |
| 2010/0179562 A1 | 7/2010 | Linker et al. |
| 2010/0324410 A1 | 12/2010 | Paek et al. |
| 2010/0331883 A1 | 12/2010 | Schmitz et al. |
| 2011/0040351 A1 | 2/2011 | Butson et al. |
| 2011/0066407 A1 | 3/2011 | Butson et al. |
| 2011/0172737 A1 | 7/2011 | Davis et al. |
| 2011/0184487 A1 | 7/2011 | Alberts et al. |
| 2011/0191275 A1 | 8/2011 | Lujan et al. |
| 2011/0196253 A1 | 8/2011 | McIntyre et al. |
| 2011/0213440 A1 | 9/2011 | Fowler et al. |
| 2011/0306845 A1 | 12/2011 | Osorio |
| 2011/0306846 A1 | 12/2011 | Osorio |
| 2011/0307032 A1 | 12/2011 | Goetz et al. |
| 2012/0046715 A1 | 2/2012 | Moffitt et al. |
| 2012/0078106 A1 | 3/2012 | Dentinger et al. |
| 2012/0089205 A1 | 4/2012 | Boyden et al. |
| 2012/0116476 A1 | 5/2012 | Kothandaraman |
| 2012/0165898 A1 | 6/2012 | Moffitt |
| 2012/0165901 A1 | 6/2012 | Zhu et al. |
| 2012/0207378 A1 | 8/2012 | Gupta et al. |
| 2012/0226138 A1 | 9/2012 | DeSalles et al. |
| 2012/0229468 A1 | 9/2012 | Lee et al. |
| 2012/0265262 A1 | 10/2012 | Osorio |
| 2012/0265268 A1 | 10/2012 | Blum et al. |
| 2012/0302912 A1 | 11/2012 | Moffitt et al. |
| 2012/0303087 A1 | 11/2012 | Moffitt et al. |
| 2012/0314924 A1 | 12/2012 | Carlton et al. |
| 2012/0316619 A1 | 12/2012 | Goetz et al. |
| 2013/0039550 A1 | 2/2013 | Blum et al. |
| 2013/0060305 A1 | 3/2013 | Bokil |
| 2013/0116748 A1 | 5/2013 | Bokil et al. |
| 2013/0116749 A1 | 5/2013 | Carlton et al. |
| 2013/0116929 A1 | 5/2013 | Carlton et al. |
| 2014/0067018 A1 | 3/2014 | Carcieri et al. |
| 2014/0277284 A1 | 9/2014 | Chen et al. |
| 2015/0134031 A1 | 5/2015 | Moffitt et al. |

FOREIGN PATENT DOCUMENTS

| | | |
|---|---|---|
| EP | 1372780 | 1/2004 |
| EP | 1559369 | 8/2005 |
| WO | 97/39797 | 10/1997 |
| WO | 98/48880 | 11/1998 |
| WO | 01/90876 A1 | 11/2001 |
| WO | 02/26314 | 4/2002 |
| WO | 02/28473 | 4/2002 |
| WO | 02/065896 | 8/2002 |
| WO | 02/072192 | 9/2002 |
| WO | 03/086185 | 10/2003 |
| WO | 2004/019799 A2 | 3/2004 |
| WO | 2004041080 | 5/2004 |
| WO | 2006017053 | 2/2006 |
| WO | 2006113305 | 10/2006 |
| WO | 2007/097859 A1 | 8/2007 |
| WO | 2007/097861 A1 | 8/2007 |
| WO | 2007/100427 A1 | 9/2007 |
| WO | 2007/100428 A1 | 9/2007 |
| WO | 2007/112061 A2 | 10/2007 |
| WO | 2009097224 | 8/2009 |
| WO | 2009097224 A1 | 8/2009 |
| WO | 2010/120823 A2 | 10/2010 |
| WO | 2011025865 | 3/2011 |

(56) References Cited

FOREIGN PATENT DOCUMENTS

| WO | 2011/139779 A1 | 11/2011 |
|---|---|---|
| WO | 2011/159688 A2 | 12/2011 |
| WO | 2012088482 | 6/2012 |

OTHER PUBLICATIONS

Butson et al., "Current Steering to Control the Volume of Tissue Activated During Deep Brain Stimulation," Brain Stimulation 1, 2008, pp. 7-15.
Butson et al., "Patient Specific Analysis of the volume of tissue activated during deep brain stimulation," NeuroImage, Academic Press, vol. 34, No. 2, Dec. 2, 2006, pp. 661-670.
Butson et al., "Role of Electrode Design on the Volume of Tissue Activated During Deep Brain Stimulation," Journal of Neural Engineering, Mar. 1, 2006, vol. 3, No. 1, pp. 1-8.
Butson et al., "StimExplorer: Deep Brain Stimulation Parameter Selection Software System," Acta Neurochirugica, Jan. 1, 2007, vol. 97, No. 2, pp. 569-574.
Miocinovic et al., "Cicerone: Stereotactic Neurophysiological Recording and Deep Brain Stimulation Electrode Placement Software System," Acta Neurochirurgica Suppl., Jan. 1, 2007, vol. 97, No. 2, pp. 561-567.
Schmidt et al., "Sketching and Composing Widgets for 3D Manipulation," Eurographics, Apr. 2008, vol. 27, No. 2, pp. 301-310.
Izad, Olivier, "Computationally Efficient Method in Predicating Axonal Excitation," Dissertation for Masters Degree, Department of Biomedical Engineering, Case Western Reserve University, May 2009, 144 pages.
Jaccard, Paul, "Étude comparative de la distribution florale dans une portion odes Aples et des Jura," Bulletin de la Société Vaudoise des Sciences Naturelles (1901), vol. 37, pp. 547-579.
Dice, Lee R., "Measures of the Amount of Ecologic Association Between Species," Ecology 26(3) (1945), pp. 297-302. doi:10.2307/1932409, http://jstor.org/stable/1932409.
Rand, W.M., "Objective criteria for the evaluation of clustering methods," Journal of the American Statistical Association (American Statistical Association) 66 (336) (1971), pp. 846-850, doi:10.2307/2284239, http://jstor.org/stable/2284239.
Hubert, Lawrence et al., "Comparing partitions," Journal of Classification 2(1) (1985), pp. 193-218, doi:10.1007/BF01908075.
Cover, T.M. et al., "Elements of information theory," (1991) John Wiley & Sons, New York, NY, pp. 1-542.
Meila, Marina, "Comparing Clusterings by the Variation of Information," Learning Theory and Kernel Machines (2003), pp. 173-187.
European Patent Office, International Search Report in International Application No. PCT/US2012/053344, dated Nov. 26, 2012, 8 pages.
European Patent Office, International Search Report in International Application No. PCT/US2012/050181, dated Jan. 3, 2013, 7 pages.
Euopean Patent Office, International Search Report and the Written Opinion in International Application No. PCT/US2012/050170, dated Oct. 5, 2012, 15 pages.
Ericsson, A. et al., "Construction of a patient-specific atlas of the brain: Application to normal aging," Biomedical Imaging: From Nano to Macro, ISBI 2008, 5th IEEE International Symposium, May 14, 2008, pp. 480-483.
Kaikai Shen et al., "Atlas selection strategy using least angle regression in multi-atlas segmentation propagation," Biomedical Imaging: From Nano to Macro, 2011, 8th IEEE International Symposium, ISBI 2011, Mar. 30, 2011, pp. 1746-1749.
Liliane Ramus et al, "Assessing selection methods in the context of multi-atlas based segmentation," Biomedical Imaging: From Nano to Macro, 2010 IEEE International Symposium, Apr. 14, 2010, pp. 1321-1324.
Olivier Commowick et al., "Using Frankenstein's Creature Paradigm to Build a Patient Specific Atlas," Sep. 20, 2009, Medical Image Computing and Computer-Assisted Intervention, pp. 993-1000.
Lotjonen J.M.P. et al, "Fast and robust multi-atlas segmentation of brain magnetic resonance images," NeuroImage, Academic Press, vol. 49, No. 3, Feb. 1, 2010, pp. 2352-2365.
Sanchez Castro et al., "A cross validation study of deep brain stimulation targeting: From experts to Atlas-Based, Segmentation-Based and Automatic Registration Algorithms," IEEE Transactions on Medical Imaging, vol. 25, No. 11, Nov. 1, 2006, pp. 1440-1450.
European Patent Office, International Search Report in International Application No. PCT/US09/03017, dated Aug. 3, 2009, 7 pages.
European Patent Office, International Search Report in International Application No. PCT/US09/03038, dated Oct. 8, 2009, 9 pages.
European Patent Office, International Search Report in International Application No. PCT/US09/03040, dated Aug. 13, 2009, 7 pages.
European Patent Office, International Search Report in International Application No. PCT/US09/03049, dated Jan. 26, 2010, 8 pages.
European Patent Office, partial International Search Report in International Application No. PCT/US2012/030701, dated Feb. 15, 2013, 7 pages.
European Patent Office, partial International Search Report in International Application No. PCT/US2012/030705, dated Mar. 6, 2013, 7 pages.
European Patent Office, International Search Report and Written Opinion in International Application No. PCT/US2012/030700, dated Feb. 27, 2013, 9 pages.
Siegel, Ralph M. et al., "Spatiotemporal dynamics of the functional architecture for gain fields in inferior parietal lobule of behaving monkey," Cerebral Cortex, New York, NY, vol. 17, No. 2, Feb. 2007, pp. 378-390.
Klein, A. et al., "Evaluation of 14 nonlinear deformation algorithms applied to human brain MRI registration," NeuroImage, Academic Press, Orlando, FL, vol. 46, No. 3, Jul. 2009, pp. 786-802.
European Patent Office, International Search report and Written Opinion in PCT application No. PCT/US12/050174, dated Mar. 6, 2013, 20 pages.
European Patent Office, International Search Report and Written Opinion in International Application No. PCT/US2012/050187, dated Feb. 27, 2013, 9 pages.
European Patent Office, International Search Report in International Application No. PCT/US09/03041, dated Aug. 20, 2009, 7 pages.
European Patent Office, International Search Report and the Written Opinion of the International Searching Authority in International Application No. PCT/US2012/050175, dated Oct. 26, 2012, 15 pages.
Nowinski, W. L., et al., "Statistical analysis of 168 bilateral subthalamic nucleus implantations by means of the probabilistic functional atlas.", Neurosurgery 57(4 Suppl) (Oct. 2005),319-30.
Obeso, J. A., et al., "Deep-brain stimulation of the subthalamic nucleus or the pars interna of the globus pallidus in Parkinson's disease.", N Engl J Med., 345{13l. The Deep-Brain Stimulation for Parkinson's Disease Study Group, (Sep. 27, 2001 ),956-63.
Fisekovic et al., "New Controller for Functional Electrical Stimulation Systems", Med. Eng. Phys. 2001; 23:391-399.
Patrick, S. K., et al., "Quantification of the UPDRS rigidity scale", IEEE Transactions on Neural Systems and Rehabilitation Engineering, [see also IEEE Trans. on Rehabilitation Engineering 9(1). (2001),31-41.
Phillips, M. D., et al., "Parkinson disease: pattern of functional MR imaging activation during deep brain stimulation of subthalamic nucleus—initial experience", Radiology 239(1). (Apr. 2006),209-16.
Merrill, D. R., et al., "Electrical stimulation of excitable tissue: design of efficacious and safe protocols", J Neurosci Methods. 141(2), (Feb. 15, 2005), 171-98.
Montgomery, E. B., et al., "Mechanisms of deep brain stimulation and future technical developments.", Neurol Res. 22(3). (Apr. 2000),259-66.
Moss, J. , et al., "Electron microscopy of tissue adherent to explanted electrodes in dystonia and Parkinson's disease", Brain, 127{Pt 12). (Dec. 2004 ),2755-63.
Hunka, K. et al., Nursing Time to Program and Assess Deep Brain Stimulators in Movement Disorder Patients, J. Neursci Nurs., 37: 204-10 (Aug. 2005).

(56) References Cited

OTHER PUBLICATIONS

Miocinovic, S., et al., "Sensitivity of temporal excitaton poperties to the neuronal element activated by exracellular stimulation", J Neuosci Methods. 132(1). (Jan. 15, 2004), 91-9.

McIntyre, C. C., et al., "How does deep brain stimulation work? Present understanding and future questions.", J Clin Neurophysiol. 21 (1 ). (Jan.-Feb. 2004 ),40-50.

Grill, W. M., "Stimulus waveforms for selective neural stimulation", IEEE Engineering in Medicine and Biology Magazine, 14(4}, (Jul.-Aug. 1995), 375-385.

Plaha, P. , et al., "Stimulation of the caudal zona incerta is superior to stimulation of the subthalamic nucleus in improving contralateral parkinsonism.", Brain 129{Pt 7) (Jul. 2006), 1732-4 7.

Rattay, F, "Analysis of models for external stimulation of axons", IEEE Trans. Biomed. Eng. vol. 33 (1986),974-977.

Rattay, F., "Analysis of the electrical excitation of CNS neurons", IEEE Transactions on Biomedical Engineering 45 (6). (Jun. 1998),766-772.

Rose, T. L., et al., "Electrical stimulation with Pt electrodes. VIII. Electrochemically safe charge injection limits with 0.2 ms pulses [neuronal application]", IEEE Transactions on Biomedical Engineering, 37(11 }, (Nov. 1990), 1118-1120.

Rubinstein, J. T., et al., "Signal coding in cochlear implants: exploiting stochastic effects of electrical stimulation", Ann Otol Rhinol Laryngol Suppl . . . 191, (Sep. 2003), 14-9.

Schwan, H.P., et al., "The conductivity of living tissues.", Ann NY Acad Sci., 65(6). (AUQ., 1957),1007-13.

Taylor, R. S., et al., "Spinal cord stimulation for chronic back and leg pain and failed back surgery syndrome: a systematic review and analysis of prognostic factors", Spine 30(1 ). (Jan. 1, 2005), 152-60.

Micheli-Tzanakou, E., et al., "Computational Intelligence for target assesment in Parkinson's disease", Proceedings of SPIE vol. 4479. Applications and Science of Neural Networks, Fuzzy Systems, and Evolutionary Computation IV,(2001),54-69.

Volkmann et al., Indroduction to the Programming of Deep Brain Stimulators, Movement Disorders, vol. 17, Suppl. 3, pp. S181-S187 (2002).

Geddes, L. A., et al., "The specific resistance of biological material—a compendium of data for the biomedical engineer and physiologist.", Med Biol Ena. 5(3). (May 1967),271-93.

Gimsa, J., et al., "Choosing electrodes for deep brain stimulation experiments-electrochemical considerations.", J Neurosci Methods, 142(2), (Mar. 30, 2005),251-65.

Vidailhet, M. , et al., "Bilateral deep-brain stimulation of the globus pallidus in primary generalized dystonia", N Engl J Med. 352(5) (Feb. 3, 2005),459-67.

Viola, P., et al., "Alignment by maximization of mutual information", International Journal of Com outer Vision 24(2). ( 1997), 137-154.

Volkmann, J., et al., "Basic algorithms for the programming of deep brain stimulation in Parkinson's disease", Mov Disord., 21 Suppl 14. (Jun. 2006)S284-9.

Walter, B. L. et al., "Surgical treatment for Parkinson's disease", Lancet Neural. 3(12). (Dec. 2004),719-28.

Wei, X. F., et al., "Current density distributions, field distributions and impedance analysis of segmented deep brain stimulation electrodes", J Neural Eng . . . 2(4). (Dec. 2005), 139-47.

Zonenshayn, M. , et al., "Location of the active contact within the subthalamic nucleus (STN) in the treatment of idiopathic Parkinson's disease.", Surg Neurol., 62(3) (Sep. 2004),216-25.

Da Silva et al (A primer on diffusion tensor imaging of anatomical substructures. Neurosurg Focus 15(1): p. 1-4, Article 4, 2003.).

Mcintyre, Cameron C., et al., "Uncovering the mechanisms of deep brain stimulation for Parkinson's disease through functional imaging, neural recording, and neural modeling," Crit Rev Biomed Eng., 30(4-6) (2002), pp. 249-281.

Mcintyre, Cameron C., et al., "Uncovering the mechanism(s) of action of deep brain stimulation: activation, inbhibition, or both," Clin Neurophysiol, 115(6) (Jun. 2004), pp. 1239-1248.

Mcintyre, C. C., et al., "Sensitivity analysis of a model of mammalian neural membrane," Biol Cybern., 79(1) (Jul. 1998), pp. 29-37.

Mcintyre, Cameron C., et al., "Selective microstimulation of central nervous system neurons," Annals of biomedical engineering, 28(3) (Mar. 2000), pp. 219-233.

Mcintyre, Cameron C., et al., "Modeling the excitability of mammalian nerve fibers: influence of aflerpotentials on the recovery cycle," J Neurophysiol, 87(2) (Feb. 2002), pp. 995-1006.

Mcintyre, C. C., et al., Model-based design of stimulus waveforms for selective microstimulation in the central nervous system,, Proceedings of the First Joint [Engineering in Medicine and Biology, 1999. 21st Annual Conf. and the 1999 Annual FallMeeting of the Biomedical Engineering Soc.] BM ES/EMBS Conference, vol. 1 (1999), p. 384.

Mcintyre, C. C., et al., "Model-based design of stimulus trains for selective microstimulation of targeted neuronal populations," Proceedings of the 23rd Annual International Conference of the IEEE Engineering in Medicine and Biology Society, vol. 1 (2001), pp. 806-809.

Mcintyre, Cameron C., et al., "Model-based Analysis of deep brain stimulation of the thalamus," Proceedings of the Second joint EMBS/BM ES Conference, vol. 3, Annual Fall Meeting of the Biomedical Engineering Society (Cal. No. 02CH37392) IEEEPiscataway, NJ (2002), pp. 2047-2048.

Mcintyre, C. C., et al., "Microstimulation of spinal motoneurons: a model study," Proceedings of the 19th Annual International Conference of the IEEE Engineering in Medicine and Biology society, vol. 5, (1997), pp. 2032-2034.

Mcintyre, C. C., et al., "Extracellular stimulation of central neurons: influence of stimulus waveform and frequency on neuronal output," J. Neurophysiol., 88(4), (Oct. 2002), pp. 1592-1604.

Liu, Haiying, et al., "Intra-operative MR-guided DBS implantation for treating PD and ET," Proceedings of SPIE vol. 4319, Department of Radiology & Neurosurgery, University of Minnesota, Minneapolis, MN 55455 (2001), pp. 272-276.

Levy, AL., et al., "An Internet-connected, patient-specific, deformable brain atlas integrated into a surgical navigation 42 system," J Digit Imaging, 10(3 Suppl 1) (Aug. 1997), pp. 231-237.

Lee, D. C., et al., "Extracellular electrical stimulation of central neurons: quantitative studies," In: Handbook of neuroprosthetic methods, WE Finn and PG Lopresti (eds) CRC Press (2003), pp. 95-125.

Le Bihan, D., et al., "Diffusion tensor imaging: concepts and applications," J Magn Reson Imaging, 13(4) (Apr. 2001), pp. 534-546.

Krack, P., et al., "Postoperative management of subthalamic nucleus stimulation for Parkinson's disease," Mov. Disord., vol. 17(suppl 3) (2002), pp. 188-197.

Jones, DK., et al., "Optimal strategies for measuring diffusion in anisotropic systems by magnetic resonance imaging," Magn. Reson. Med., 42(3) (Sep. 1999), pp. 515-525.

Jezernik, S., et al., "Neural network classification of nerve activity recorded in a mixed nerve," Neurol Res., 23(5) (Jul. 2001), pp. 429-434.

Holsheimer, J., et al., "Identification of the target neuronal elements in electrical deep brain stimulation," Eur J Neurosci., 12(12) (Dec. 2000), pp. 4573-4577.

Hoekema, R., et al., "Multigrid solution of the potential field in modeling electrical nerve stimulation," Comput Biomed Res., 31(5) (Oct. 1998), pp. 348-362.

Hodaie, M., et al., "Chronic anterior thalamus stimulation for intractable epilepsy," Epilepsia, 43(6) (Jun. 2002), pp. 603-608.

Zhang, Y., et al., "Atlas-guided tract reconstruction for automated and comprehensive examination of the white matter anatomy," Neuroimage 52(4) (2010), pp. 1289-1301.

""BioPSE" The Biomedical Problem Solving Environment", htt12://www.sci.utah.edu/cibc/software/index.html, MCRR Center for Integrative Biomedical Computing,(2004).

Andrews, R. J., "Neuroprotection trek—the next generation: neuromodulation I. Techniques—deep brain stimulation, vague nerve stimulation, and transcranial magnetic stimulation.", Ann NY Acad Sci. 993. (May 2003),1-13.

(56) References Cited

OTHER PUBLICATIONS

Carnevale, N.T. et al., "The Neuron Book," Cambridge, UK: Cambridge University Press (2006), 480 pages.

Chaturvedi: "Development of Accurate Computational Models for Patient-Specific Deep Brain Stimulation," Electronic Thesis or Dissertation, Jan. 2012, 162 pages.

Chaturvedi, A. et al.: "Patient-specific models of deep brain stimulation: Influence of field model complexity on neural activation predictions." Brain Stimulation, Elsevier, Amsterdam, NL, vol. 3, No. 2 Apr. 2010, pp. 65-77.

Frankemolle, et al., "Reversing cognitive-motor impairments in Parkinson's disease patients using a computational modeling approach to deep brain stimulation programming," Brian 133 (2010), pp. 746-761.

McIntyre, C.C., et al., "Modeling the excitablitity of mammalian nerve fibers: influence of afterpotentials on the recovery cycle," J Neurophysiol, 87(2) (Feb. 2002), pp. 995-1006.

Peterson, et al., "Predicting myelinated axon activation using spatial characteristics of the extracellular field," Journal of Neural Engineering, 8 (2011), 12 pages.

Warman, et al., "Modeling the Effects of Electric Fields on nerver Fibers; Dermination of Excitation Thresholds,"IEEE Transactions on Biomedical Engineering, vol. 39, No. 12 (Dec. 1992), pp. 1244-1254.

Wesselink, et al., "Analysis of Current Density and Related Parameters in Spinal Cord Stimulation," IEEE Transactions on Rehabilitation Engineering, vol. 6, No. 2 Jun. 1998, pp. 200-207.

Andrews, R. J., "Neuroprotection trek—the next generation: neuromodulation II. Applications—epilepsy, nerve regeneration, neurotrophins.", NY Acad Sci. 993 (May 2003), 14-24.

Astrom, M. , et al., "The effect of cystic cavities on deep brain stimulation in the basal ganglia: a simulation-based study", J Neural Eng., 3(2), (Jun. 2006). 132-8.

Mouine et al. "Multi-Strategy and Multi-Algorithm Cochlear Prostheses", Biomed. Sci. Instrument, 2000; 36:233-238.

Back, C. , et al., "Postoperative Monitoring of the Electrical Properties of Tissue and Electrodes in Deep Brain Stimulation", Neuromodulation, 6(4), (Oct. 2003 ),248-253.

Baker, K. B., et al., "Evaluation of specific absorption rate as a dosimeter of MRI-related implant heating", J Magn Reson Imaging., 20(2), (Aug. 2004),315-20.

Brown, J. "Motor Cortex Stimulation," Neurosurgical Focus ( Sep. 15, 2001) 11(3):E5.

Budai et al., "Endogenous Opioid Peptides Acting at m-Opioid Receptors in the Dorsal Horn Contribute to Midbrain Modulation of Spinal Nociceptive Neurons," Journal of Neurophysiology (1998) 79(2): 677-687.

Cesselin, F. "Opioid and anti-opioid peptides," Fundamental and Clinical Pharmacology (1995) 9(5): 409-33 (Abstract only).

Rezai et al., "Deep Brain Stimulation for Chronic Pain" Surgical Management of Pain, Chapter 44 pp. 565-576 (2002).

Xu, MD., Shi-Ang, article entitled "Comparison of Half-Band and Full-Band Electrodes for Intracochlear Electrical Stimulation", Annals of Otology, Rhinology & Laryngology (Annals of Head & Neck Medicine & Surgery), vol. 102 (5) pp. 363-367 May 1993.

Bedard, C. , et al., "Modeling extracellular field potentials and the frequency-filtering properties of extracellular space", Biophys J . . . 86(3). (Mar. 2004), 1829-42.

Benabid, A. L., et al., "Future prospects of brain stimulation", Neurol Res.;22(3), (Apr. 2000),237-46.

Brummer, S. B., et al., "Electrical Stimulation with Pt Electrodes: II—Estimation of Maximum Surface Redox (Theoretical Non-Gassing) Limits", IEEE Transactions on Biomedical Engineering, vol. BME-24, Issue 5, (Sep. 1977),440-443.

Butson, Christopher R., et al., "Deep Brain Stimulation of the Subthalamic Nucleus: Model-Based Analysis of the Effects of Electrode Capacitance on the Volume of Activation", Proceedings of the 2nd International IEEE EMBS, (Mar. 16-19, 2005),196-197.

Mcintyre, Cameron C., et al., "Cellular effects of deep brain stimulation: model-based analysis of activation and inhibition," J Neurophysiol, 91(4) (Apr. 2004), pp. 1457-1469.

Chaturvedi, A., et al., "Subthalamic Nucleus Deep Brain Stimulation: Accurate Axonal Threshold Prediction with Diffusion Tensor Based Electric Field Models", Engineering in Medicine and Biology Society, 2006. EMBS' 06 28th Annual International Conference of the IEEE, IEEE, Piscataway, NJ USA, Aug. 30, 2006.

Butson, Christopher et al., "Predicting the Effects of Deep Brain Stimulation with Diffusion Tensor Based Electric Field Models" Jan. 1, 2001, Medical Image Computing and Computer-Assisted Intervention-Mic CAI 2006 Lecture Notes in Computer Science; LNCS, Springer, Berlin, DE.

Butson, C. R., et al., "Deep brainstimulation interactive visualization system", Society for Neuroscience vol. 898.7 (2005).

Grill, WM., et al., "Electrical properties of implant encapsulation tissue", Ann Biomed Eng. vol. 22. (1994),23-33.

McNaughtan et al., "Electrochemical Issues in Impedance Tomography", 1st World Congress on Industrial Process Tomography, Buxton, Greater Manchester, Apr. 14-17, 1999.

Hardman, C. D., et al., "Comparison of the basal ganglia in rats, marmosets, macaques, baboons, and humans: volume and neuronal number for the output, internal relay, and striatal modulating nuclei", J Comp Neurol., 445(3). (Apr. 8, 2002),238-55.

Hashimoto, T. , et al., "Stimulation of the subthalamic nucleus changes the firing pattern of pallidal neurons", J Neurosci. 23(5). (Mar. 1, 2003),1916-23.

Haslinger, B., et al., "Frequency-correlated decreases of motor cortex activity associated with subthalamic nucleus stimulation in Parkinson's disease.", Neuroimage 28(3). (Nov. 15, 2005),598-606.

Haueisen, J. et al., "The influence of brain tissue anisotropy on human EEG and MEG", Neuroimage 15(1) (Jan. 2002),159-166.

Hemm, S., et al., "Deep brain stimulation in movement disorders: stereotactic coregistration of two-dimensional electrical field modeling and magnetic resonance imaging.", J Neurosurg. 103(6), (Dec. 2005),949-55.

Hemm, S. , et al., "Evolution of Brain Impedance in Dystonic Patients Treated by GPi Electrical Stimulation", Neuromodulation 7(2) (Apr. 2004),67-75.

Hershey, T., et al., "Cortical and subcortical blood flow effects of subthalamic nucleus stimulation in PD.", Neurology 61(6). (Sep. 23, 2003),816-21.

Herzog, J., et al., "Most effective stimulation site in subthalamic deep brain stimulation for Parkinson's disease". Mov Disord. 19(9). (Sep. 2004),1050-4.

Hines, M. L., et al., "The Neuron simulation environment", Neural Comput. 9(6). (Aug. 15, 1997), 1179-209.

Johnson, M. D., et al., "Repeated voltage biasing improves unit recordings by reducing resistive tissue impedances", IEEE Transactions on Neural Systems and Rehabilitation Engineering, [see also IEEE Trans. on Rehabilitation Engineering (2005), 160-165.

Kitagawa, M., et al., "Two-year follow-up of chronic stimulation of the posterior subthalamic white matter for tremor-dominant Parkinson's disease.", Neurosurgery. 56(2). (Feb. 2005),281-9.

Limousin, P., et al., "Electrical stimulation of the subthalamic nucleus in advanced Parkinson's disease", N Engl J Med . . . 339(16), (Oct. 15, 1998), 1105-11.

Foster, K. R., et al., "Dielectric properties of tissues and biological materials: a critical review.", Grit Rev Biomed Ena. 17 (1 ). (1989),25-104.

McIntyre, Cameron , et al., "Finite element analysis of the current-density and electric field generated by metal microelectrodes", Ann Biomed Eng . 29(3), (2001 ),227-235.

Mayr et al., "Basic Design and Construction of the Vienna FES Implants: Existing Solutions and Prospects for New Generations of Implants", Medical Engineering & Physics, 2001; 23:53-60.

Wakana, S., et al., "Reproducibility of quantitative tractography methods applied to cerebral white matter," Neuroimage 36 (3) (2007), pp. 630-644.

Viola, et al., "Importance-driven focus of attention," IEEE Trans Vis Comput Graph 12 (5) (2006), pp. 933-940.

Saxena, et al., "Cerebral glucose metabolism in obsessive-compulsive hoarding," Am J Psychiatry. 161 (6) (2004), pp. 1038-1048.

(56) References Cited

OTHER PUBLICATIONS

Mcintyre, Cameron C., et al., "Electric Field and Stimulating Influence generated by Deep Brain Stimulation of the Subthalamaic Nucleus," Clinical Neurophysiology, 115(3) (Mar. 2004), pp. 589-595.

Mcintyre, Cameron C., et al., "Electric field generated by deep brain stimulation of the subthalamic nucleus," Biomedical Engineering Society Annual Meeting, Nashville TN (Oct. 2003), 16 pages.

Mcintyre, Cameron C., et al., "Excitation of central nervous system neurons by nonuniform electric fields," Biophys. J., 76(2) (1999), pp. 878-888.

McNeal, Dr., et al., "Analysis of a model for excitation of myelinated nerve," IEEE Trans Biomed Eng., vol. 23 (1976), pp. 329-337.

Micheli-Tzanakou, E., et al., "Computational Intelligence for target assesment in Parkinson's disease," Proceedings of SPIE vol. 4479, Applications and Science of Neural Networks, Fuzzy Systems, and Evolutionary Computation IV (2001), pp. 54-69.

Miocinovic, S., et al., "Computational analysis of subthalamic nucleus and lenticular fasciculus activation during therapeutic deep brain stimulation," J Neurophysiol., 96(3) (Sep. 2006), pp. 1569-1580.

Miranda, P. C., et al., "The distribution of currents inducedin the brain by Magnetic Stimulation: a finite element analysis incorporating OT-MRI-derived conductivity data," Proc. Intl. Soc. Mag. Reson. Med. 9 (2001), p. 1540.

Miranda, P. C., et al., "The Electric Field Induced in the Brain by Magnetic Stimulation: A 3-D Finite-Element Analysis of the Effect of Tissue Heterogeneity and Anisotropy," IEEE Transactions on Biomedical Engineering, 50(9) (Sep. 2003), pp. 1074-1085.

Moffitt, MA., et al. "Prediction of myelinated nerve fiber stimulation thresholds: limitations of linear models," IEEE Transactions on Biomedical Engineering, 51 (2) (2003), pp. 229-236.

Moro, E, et al., "The impact on Parkinson's disease of electrical parameter settings in STN stimulation," Neurology, 59 (5) (Sep. 10, 2002), pp. 706-713.

Nowak, LG., et al., "Axons, but not cell bodies, are activated by electrical stimulation in cortical gray matter. I. Evidence from chronaxie measurements," Exp. Brian Res., 118(4) (Feb. 1998), pp. 477-488.

Nowak, LG., et al., "Axons, but not cell bodies, are activated by electrical stimulation in cortical gray matter. II. Evidence from selective inactivation of cell bodies and axon initial segments," Exp. Brain Res., 118(4) (Feb. 1998), pp. 489-500.

O'Suilleabhain, PE., et al., "Tremor response to polarity, voltage, pulsewidth and frequency of thalamic stimulation," Neurology, 60(5) (Mar. 11, 2003), pp. 786-790.

Pierpaoli, C., et al., "Toward a quantitative assessment of diffusion anisotropy," Magn Reson Med., 36(6) (Dec. 1996), pp. 893-906.

Plonsey, R., et al., "Considerations of quasi-stationarity in electrophysiological systems," Bull Math Biophys., 29(4) (Dec. 1967), pp. 657-664.

Ranck, J B., "Specific impedance of rabbit cerebral cortex," Exp. Neurol., vol. 7 (Feb. 1963), pp. 144-152.

Ranck, J B., et al., "The Specific impedance of the dorsal columns of the cat: an anisotropic medium," Exp. Neurol., 11 (Apr. 1965), pp. 451-463.

Ranck, J B., "Which elements are excited in electrical stimulation of mammalian central nervous system: a review," Brain Res., 98(3) (Nov. 21, 1975), pp. 417-440.

Rattay, F., et al., "A model of the electrically excited human cochlear neuron. I. Contribution of neural substructures to the generation and propagation of spikes," Hear Res., 153(1-2)(Mar. 2001), pp. 43-63.

Rattay, F., "A model of the electrically excited human cochlear neuron. II. Influence of the three-dimensional cochlear structure on neural excitability," Hear Res., 153(1-2) (Mar. 2001), pp. 64-79.

Rattay, F., "Arrival at Functional Electrostimulation by modeling of fiber excitation," Poceedings of the Ninth annual Conference of the IEEE Engineering in Medicine and Biology Society (1987), pp. 1459-1460.

Rattay, F., "The influence of intrinsic noise can preserve the temporal fine structure of speech signals in models of electrically stimulated human cochlear neurones," Journal of Physiology, Scientific Meeting of the Physiological Society, London, England, UK Apr. 19-21, 1999 (Jul. 1999), p. 170P.

Rizzone, M., et al., "Deep brain stimulation of the subthalamic nucleus in Parkinson's disease: effects of variation in stimulation parameters," J. Neurol. Neurosurg. Psychiatry., 71(2) (Aug. 2001), pp. 215-219.

Saint-Cyr, J. A., et al., "Localization of clinically effective stimulating electrodes in the human subthalamic nucleus on magnetic resonance imaging," J. Neurosurg., 87(5) (Nov. 2002), pp. 1152-1166.

Sances, A., et al., "In Electroanesthesia: Biomedical and Biophysical Studies," A Sances and SJ Larson, Eds., Academic Press, NY (1975), pp. 114-124.

SI. Jean, P., et al., "Automated atlas integration and interactive three-dimensional visualization tools for planning and guidance in functional neurosurgery," IEEE Transactions on Medical Imaging, 17(5) (1998), pp. 672-680.

Starr, P.A., et al., "Implantation of deep brain stimulators into the subthalamic nucleus: technical approach and magnetic resonance imaging-verified lead locations," J. Neurosurg., 97(2) (Aug. 2002), pp. 370-387.

Sterio, D., et al., "Neurophysiological refinement of subthalamic nucleus targeting," Neurosurgery, 50(1) (Jan. 2002), pp. 58-69.

Struijk, J. J., et al., "Excitation of dorsal root fibers in spinal cord stimulation: a theoretical study," IEEE Transactions on Biomedical Engineering, 40(7) (Jul. 1993), pp. 632-639.

Struijk, J J., et al., "Recruitment of dorsal column fibers in spinal cord stimulation: influence of collateral branching," IEEE Transactions on Biomedical Engineering, 39(9) (Sep. 1992), pp. 903-912.

Tamma, F., et al., "Anatomo-clinical correlation of intraoperative stimulation-induced side-effects during HF-DBS of the subthalamic nucleus," Neurol Sci., vol. 23 (Suppl 2) (2002), pp. 109-110.

Tarler, M., et al., "Comparison between monopolar and tripolar configurations in chronically implanted nerve cuff electrodes," IEEE 17th Annual Conference Engineering in Medicine and Biology Society, vol. 2 (1995), pp. 1093-109.

Testerman, Roy L., "Coritical response to callosal stimulation: A model for determining safe and efficient stimulus parameters," Annals of Biomedical Engineering, 6(4) (1978), pp. 438-452.

Tuch, D.S., et al., "Conductivity mapping of biological tissue using diffusion MRI," Ann NY Acad Sci., 888 (Oct. 30, 1999), pp. 314-316.

Tuch, D.S., et al., "Conductivity tensor mapping of the human brain using diffusion tensor MRI," Proc Nall Acad Sci USA, 98(20) (Sep. 25, 2001), pp. 11697-11701.

Veraart, C., et al., "Selective control of muscle activation with a multipolar nerve cuff electrode," IEEE Transactions on Biomedical Engineering, 40(7) (Jul. 1993), pp. 640-653.

Vercueil, L., et al., "Deep brain stimulation in the treatment of severe dystonia," J. Neurol., 248(8) (Aug. 2001), pp. 695-700.

Vilalte, "Circuit Design of the Power-on-Reset," Apr. 2000, pp. 1-25.

Vitek, J. L., "Mechanisms of deep brain stimulation: excitation or inhibition," Mov. Disord., vol. 17 (Suppl. 3) (2002), pp. 69-72.

Voges, J., et al., "Bilateral high-frequency stimulation in the subthalamic nucleus for the treatment of Parkinson disease: correlation of therapeutic effect with anatomical electrode position," J. Neurosurg., 96(2) (Feb. 2002), pp. 269-279.

Wakana, S., et al., "Fiber tract-based atlas of human white matter anatomy," Radiology, 230(1) (Jan. 2004), pp. 77-87.

Alexander, DC., et al., "Spatial transformations of diffusion tensor magnetic resonance images," IEEE Transactions on Medical Imaging, 20 (11), (2001), pp. 1131-1139.

Wu, Y. R., et al., "Does Stimulation of the GPi control dyskinesia by activating inhibitory axons?," Mov. Disord., vol. 16 (2001), pp. 208-216.

(56) References Cited

OTHER PUBLICATIONS

Yelnik, J., et al., "Localization of stimulating electrodes in patients with Parkinson disease by using a three-dimensional atlas-magnetic resonance imaging coregistration method," J Neurosurg., 99(1) (Jul. 2003), pp. 89-99.
Yianni, John, et al., "Globus pallidus internus deep brain stimulation for dystonic conditions: a prospective audit," Mov. Disord., vol. 18 (2003), pp. 436-442.
Zonenshayn, M., et al., "Comparison of anatomic and neurophysiologica methods for subthalamic nucleus targeting," Neurosurgery, 47(2) (Aug. 2000), pp. 282-294.
Voghell et al., "Programmable Current Source Dedicated to Implantable Microstimulators" ICM '98 Proceedings of the Tenth International Conference, pp. 67-70.
Grill, W. M., et al., "Deep brain stimulation creates an informational lesion of the stimulated nucleus", Neuroreport. 15l7t (May 19, 2004 ), 1137-40.
Adler, DE., et al., "The tentorial notch: anatomical variation, morphometric analysis, and classification in 100 human autopsy cases," J. Neurosurg., 96(6), (Jun. 2002), pp. 1103-1112.
Jones et al., "An Advanced Demultiplexing System for Physiological Stimulation", IEEE Transactions on Biomedical Engineering, vol. 44 No. 12 Dec. 1997, pp. 1210-1220.
Alo, K. M., et al., "New trends in neuromodulation for the management of neuropathic pain," Neurosurgery, 50(4), (Apr. 2002), pp. 690-703, discussion pp. 703-704.
Ashby, P., et al., "Neurophysiological effects of stimulation through electrodes in the human subthalamic nucleus," Brain, 122 (PI 10), (Oct. 1999), pp. 1919-1931.
Baker, K. B., et al., "Subthalamic nucleus deep brain stimulus evoked potentials: Physiological and therapeutic implications," Movement Disorders, 17(5), (Sep./Ocl. 2002), pp. 969-983.
Bammer, R, et al., "Diffusion tensor imaging using single-shot SENSE-EPI", Magn Reson Med., 48(1 ), (Jul. 2002), pp. 128-136.
Basser, P J., et al., "MR diffusion tensor spectroscopy and imaging," Biophys J., 66(1 ), (Jan. 1994), pp. 259-267.
Basser, P J., et al., "New currents in electrical stimulation of excitable tissues," Annu Rev Biomed Eng., 2, (2000), pp. 377-397.
Benabid, AL., et al., "Chronic electrical stimulation of the ventralis intermedius nucleus of the thalamus as a treatment of movement disorders," J. Neurosurg., 84(2), (Feb. 1996), pp. 203-214.
Benabid , AL., et al., "Combined (Ihalamotoy and stimulation) stereotactic surgery of the VIM thalamic nucleus for bilateral Parkinson disease," Appl Neurophysiol, vol. 50, (1987), pp. 344-346.
Benabid, A L., et al., "Long-term suppression of tremor by chronic stimulation of the ventral intermediate thalamic nucleus," Lancet, 337 (8738), (Feb. 16, 1991 ), pp. 403-406.
Nuttin, et al., "Electrical stimulation in anterior limbs of internal capsules in patients with obsessive-compulsive disorder," Lancet 354 (9189) (1999), p. 1526.
Christensen Gary E., et al., "Volumetric transformation of brain anatomy," IEEE Transactions on Medical Imaging, 16(6), (Dec. 1997), pp. 864-877.
Cooper, S , et al., "Differential effects of thalamic stimulation parameters on tremor and paresthesias in essential tremor," Movement Disorders, 17(Supp. 5), (2002), p. S193.
Coubes, P, et al., "Treatment of DYT1-generalised dystonia by stimulation of the internal globus pallidus," Lancet, 355 (9222), (Jun. 24, 2000), pp. 2220-2221.
Miocinovic, S., et al., "Experimental and theoretical characterization of the voltage distribution generated by deep brain stimulation," Exp Neurol 216 (i) (2009), pp. 166-176.
Goodall, E. V., et al., "Position-selective activation of peripheral nerve fibers with a cuff electrode," IEEE Transactions on Biomedical Engineering, 43(8) (Aug. 1996), pp. 851-856.
Finnis, K. W., et al., "3-D functional atalas of subcortical structures for image guided stereotactic neurosurgery," Neuroimage, vol. 9 No. 6, Iss. 2 (1999), p. S206.

Finnis, K. W., et al., "3D Functional Database of Subcorticol Structures for Surgical Guidance in Image Guided Stereotactic Neurosurgery," Medical Image Computing and Computer-Assisted Intervention—MICCAI'99, Second International Conference.Cambridge, UK, Sep. 19-22, 1999, Proceedings (1999), pp. 758-767.
Finnis, K. W., et al., "A 3-Dimensional Database of Deep Brain Functional Anatomy, and Its Application to Image-Guided Neurosurgery," Proceedings of the Third International Conference on Medical Image Computing and Computer-Assisted Intervention. Lecture Notes in Computer Science; vol. 1935 (2000), pp. 1-8.
Finnis, K. W., et al., "A functional database for guidance of surgical and therapeutic procedures in the deep brain," Proceedings of the 22nd Annual International Conference of the IEEE Engineering in Medicine and Biology Society, vol. 3 (2000), pp. 1787-1789.
Finnis, K. W., et al., "Application of a Population Based Electrophysiological Database to the Planning and Guidance of Deep Brain Stereotactic Neurosurgery," Proceedings of the 5th International Conference on Medical Image Computing and Computer-Assisted Intervention-Part 11, Lecture Notes in Computer Science; vol. 2489 (2002), pp. 69-76.
Finnis, K. W., et al., "Subcortical physiology deformed into a patient-specific brain atlas for image-guided stereotaxy," Proceedings of SPIE—vol. 4681 Medical Imaging 2002: Visualization, Image-Guided Procedures, and Display (May 2002), pp. 184-195.
Finnis, Krik W., et al., "Three-Dimensional Database of Subcortical Electrophysiology for Image-Guided Stereotatic Functional Neurosurgery," IEEE Transactions on Medical Imaging, 22(1) (Jan. 2003), pp. 93-104.
Gabriels, L , et al., "Deep brain stimulation for treatment-refractory obsessive-compulsive disorder: psychopathological and neuropsychological outcome in three cases," Acta Psychiatr Scand., 107(4) (2003), pp. 275-282.
Gabriels, LA., et al., "Long-term electrical capsular stimulation in patients with obsessive-compulsive disorder," Neurosurgery, 52(6) (Jun. 2003), pp. 1263-1276.
Goodall, E. V., et al., "Modeling study of activation and propagation delays during stimulation of peripheral nerve fibers with a tripolar cuff electrode," IEEE Transactions on Rehabilitation Engineering, [see also IEEE Trans. on Neural Systems and Rehabilitation], 3(3) (Sep. 1995), pp. 272-282.
Goodall, E. V., "Simulation of activation and propagation delay during tripolar neural stimulation," Proceedings of the 15th Annual International Conference of the IEEE Engineering in Medicine and Biology Society (1993), pp. 1203-1204.
Grill, WM., "Modeling the effects of electric fields on nerve fibers: influence of tissue electrical properties," IEEE Transactions on Biomedical Engineering, 46(8) (1999), pp. 918-928.
Grill, W. M., et al., "Neural and connective tissue response to long-term implantation of multiple contact nerve cuff electrodes," J Biomed Mater Res., 50(2) (May 2000), pp. 215-226.
Grill, W. M., "Neural modeling in neuromuscular and rehabilitation research," Proceedings of the 23rd Annual International Conference of the IEEE Engineering in Medicine and Biology Society, vol. 4 (2001 ), pp. 4065-4068.
Grill, W. M., et al., "Non-invasive measurement of the input-output properties of peripheral nerve stimulating electrodes," Journal of Neuroscience Methods, 65(1) (Mar. 1996), pp. 43-50.
Grill, W. M., et al., "Quantification of recruitment properties of multiple contact cuff electrodes," IEEE Transactions on Rehabilitation Engineering, [see also IEEE Trans. on Neural Systems and Rehabilitation], 4(2) (Jun. 1996), pp. 49-62.
Grill, W. M., "Spatially selective activation of peripheral nerve for neuroprosthetic applications," Ph.D. Case Western Reserve University, (1995), pp. 245 pages.
Grill, W. M., "Stability of the input-output properties of chronically implanted mulitple contact nerve cuff stimulating electrodes," IEEE Transactions on Rehabilitation Engineering [see also IEEE Trans. on Neural Systems and Rehabilitation] (1998), pp. 364-373.
Grill, W. M., "Stimulus waveforms for selective neural stimulation," IEEE Engineering in Medicine and Biology Magazine, 14(4) (Jul.-Aug. 1995), pp. 375-385.

(56) References Cited

OTHER PUBLICATIONS

Grill, W. M., et al., "Temporal stability of nerve cuff electrode recruitment properties," IEEE 17th Annual Conference Engineering in Medicine and Biology Society, vol. 2 (1995), pp. 1089-1090.
Gross, RE., et al., "Advances in neurostimulation for movement disorders," Neurol Res., 22(3) (Apr. 2000), pp. 247-258.
Guridi et al., "The subthalamic nucleus, hemiballismus and Parkinson's disease: reappraisal of a neurological dogma," Brain, vol. 124, 2001, pp. 5-19.
Haberler, C. et al., "No tissue damage by chronic deep brain stimulation in Parkinson's disease," Ann Neurol., 48(3) (Sep. 2000), pp. 372-376.
Hamel, W, et al., "Deep brain stimulation of the subthalamic nucleus in Parkinson's disease: evaluation of active electrode contacts," J Neurol Neurosurg Psychiatry, 74(8) (Aug. 2003), pp. 1036-1046.
Hanekom, "Modelling encapsulation tissue around cochlear implant electrodes," Med. Biol. Eng. Comput. vol. 43 (2005), pp. 47-55.
Haueisen, J , et al., "The influence of brain tissue anisotropy on human EEG and MEG," Neuroimage, 15(1) (Jan. 2002), pp. 159-166.
D'Haese et al. Medical Image Computing and Computer-Assisted Intervention—MICCAI 2005 Lecture Notes in Computer Science, 2005, vol. 3750, 2005, 427-434.
Rohde et al. IEEE Transactions on Medical Imaging, vol. 22 No. 11, 2003 p. 1470-1479.
Dawant et al., Biomedical Image Registration. Lecture Notes in Computer Science, 2003, vol. 2717, 2003, 142-150.
Miocinovic et al., "Stereotactiv Neurosurgical Planning, Recording, and Visualization for Deep Brain Stimulation in Non-Human Primates", Journal of Neuroscience Methods, 162:32-41, Apr. 5, 2007, XP022021469.
Gemmar et al., "Advanced Methods for Target Navigation Using Microelectrode Recordings in Stereotactic Neurosurgery for Deep Brain Stimulation", 21st IEEE International Symposium on Computer-Based Medical Systems, Jun. 17, 2008, pp. 99-104, XP031284774.
Acar et al., "Safety Anterior Commissure-Posterior Commissure-Based Target Calculation of the Subthalamic Nucleus in Functional Stereotactiv Procedures", Stereotactic Funct. Neurosura., 85:287-291, Aug. 2007.
Andrade-Souza, "Comparison of Three Methods of Targeting the Subthalamic Nucleus for Chronic Stimulation in Parkinson's Disease", Neurosurgery, 56:360-368, Apr. 2005.
Anheim et al., "Improvement in Parkinson Disease by Subthalamic Nucleus Stimulation Based on Electrode Placement", Arch Neural., 65:612-616, May 2008.
Butson et al., "Tissue and Electrode Capacitance Reduce Neural Activation Volumes During Deep Brain Stimulation", Clinical Neurophysiology, 116:2490-2500, Oct. 2005.
Butson et al., "Sources and Effects of Electrode Impedance During Deep Brain Stimulation", Clinical Neurophysiology, 117:44 7-454, Dec. 2005.
D'Haese et al., "Computer-Aided Placement of Deep Brain Stimulators: From Planning to Intraoperative Guidance", IEEE Transaction on Medical Imaging, 24:1469-1478, Nov. 2005.
Gross et al., "Electrophysiological Mapping for the Implantation of Deep Brain Stimulators for Parkinson's Disease and Tremor", Movement Disorders, 21 :S259-S283, Jun. 2006.
Halpern et al., "Brain Shift During Deep Brain Stimulation Surgery for Parkinson's Disease", Stereotact Funct. Neurosurg., 86:37-43, published online Sep. 2007.
Herzog et al., "Most Effective Stimulation Site in Subthalamic Deep Brain Stimulation for Parkinson's Disease", Movement Disorders, 19:1050-1099, published on line Mar. 2004.
Jeon et al., A Feasibility Study of Optical Coherence Tomography for Guiding Deep Brain Probes, Journal of Neuroscience Methods, 154:96-101, Jun. 2006.
Khan et al., "Assessment of Brain Shift Related to Deep Brain. Stimulation Surgery", Sterreotact Funct. Neurosurg., 86:44-53, published online Sep. 2007.
Koop et al., "Improvement in a Quantitative Measure of Bradykinesia After Microelectrode Recording in Patients with Parkinson's Disease During Deep Brain Stimulation Surgery", Movement Disorders, 21 :673-678, published on line Jan. 2006.
Lemaire et al., "Brain Mapping in Stereotactic Surgery: A Brief Overview from the Probabilistic Targeting to the Patient-Based Anatomic Mapping", NeuroImage, 37:S109-S115, available online Jun. 2007.
Machado et al., "Deep Brain Stimulation for Parkinson's Disease: Surgical Technique and Perioperative Management", Movement Disorders, 21 :S247-S258, Jun. 2006.
Maks et al., "Deep Brain Stimulation Activation Volumes and Their Association with Neurophysiological Mapping and Therapeutic Outcomes", Downloaded from jnnp.bmj.com, pp. 1-21, published online Apr. 2008.
Moran et al., "Real-Time Refinment of Subthalamic Nucleous Targeting Using Bayesian Decision-Making on the Root Mean Square Measure", Movement Disorders, 21: 1425-1431, published online Jun. 2006.
Sakamoto et al., "Homogeneous Fluorescence Assays for RNA Diagnosis by Pyrene-Conjugated 2'-0-Methyloligoribonucleotides", Nucleosides, Nucleotides, and Nucleric Acids, 26:1659-1664, on line publication Oct. 2007.
Winkler et al., The First Evaluation of Brain Shift During Functional Neurosurgery by Deformation Field Analysis, J. Neural. Neurosurg. Psychiatry, 76:1161-1163, Aug. 2005.
Yelnik et al., "A Three-Dimensional, Histological and Deformable Atlas of the Human Basal J Ganglia. I. Atlas Construction Based on Immunohistochemical and MRI Data", NeuroImage, 34:618,-638,Jan. 2007.
Ward, H. E., et al., "Update on deep brain stimulation for neuropsychiatric disorders," Neurobiol Dis 38 (3) (2010), pp. 346-353.
Alberts et al. "Bilateral subthalamic stimulation impairs cognitive-motor performance in Parkinson's disease patients." Brain (2008), 131, 3348-3360, Abstract.
Mayberg, H. S., et al., "Deep brain stimulation for treatment-resistant depression," Neuron, 45(5) (Mar. 3, 2005), pp. 651-660.
An, et al., "Prefronlal cortical projections to longitudinal columns in the midbrain periaqueductal gray in macaque monkeys," J Comp Neural 401 (4) (1998), pp. 455-479.
Mayberg, H. S., et al., "Limbic-cortical dysregulation: a proposed model of depression," J Neuropsychiatry Clin Neurosci. 9 (3) (1997), pp. 471-481.
Carmichael, S. T., et al., "Connectional networks within the orbital and medial prefronlal cortex of macaque monkeys," J Comp Neural 371 (2) (1996), pp. 179-207.
Croxson, et al., "Quantitative investigation of connections of the prefronlal cortex in the human and macaque using probabilistic diffusion tractography," J Neurosci 25 (39) (2005), pp. 8854-8866.
Frankemolle, et al., "Reversing cognitive-motor impairments in Parkinson's disease patients using a computational modelling approach to deep brain stimulation programming," Brain 133 (2010), pp. 746-761.
Freedman, et al., "Subcortical projections of area 25 (subgenual cortex) of the macaque monkey," J Comp Neurol 421 (2) (2000), pp. 172-188.
Giacobbe, et al., "Treatment resistant depression as a failure of brain homeostatic mechanisms: implications for deep brain stimulation," Exp Neural 219 (1) (2009), pp. 44-52.
Goodman, et al., "Deep brain stimulation for intractable obsessive compulsive disorder: pilot study using a blinded, staggered-onset design," Biol Psychiatry 67 (6) (2010), pp. 535-542.
Greenberg, et al., "Deep brain stimulation of the ventral internal capsule/ventral striatum for obsessive-compulsive disorder: worldwide experience," Mol Psychiatry 15 (1) (2010), pp. 64-79.
Greenberg. et al., "Three-year outcomes in deep brain stimulation for highly resistant obsessive-compulsive disorder," Neuropsychopharmacology 31 (11) (2006), pp. 2384-2393.
Gutman, et al., "A tractography analysis of two deep brain stimulation white matter targets for depression," Biol Psychiatry 65 (4) (2009), pp. 276-282.

(56) References Cited

OTHER PUBLICATIONS

Haber, et al., "Reward-related cortical inputs define a large striatal region in primates that interface with associative cortical connections, providing a substrate for incentive-based learning," J Neurosci 26 (32) (2006), pp. 8368-8376.

Haber, et al., "Cognitive and limbic circuits that are affected by deep brain stimulation," Front Biosci 14 (2009), pp. 1823-1834.

McIntyre, C. C., et al., "Network perspectives on the mechanisms of deep brain stimulation," Neurobiol Dis 38 (3) (2010), pp. 329-337.

Hua, et al., "Tract probability maps in stereotaxic spaces: analyses of white matter anatomy and tract-specific quantification," Neuroimage 39 (1) (2008), pp. 336-347.

Johansen-Berg, et al., "Anatomical connectivity of the subgenual cingulate region targeted with deep brain stimulation for treatment-resistant depression," Cereb Cortex 18 (6) (2008), pp. 1374-1383.

Kopell, et al., "Deep brain stimulation for psychiatric disorders," J Clin Neurophysiol 21 (1) (2004), pp. 51-67.

Lozano, et al., "Subcallosal cingulate gyrus deep brain stimulation for treatment-resistant depression," Biol Psychiatry 64 (6) (2008), pp. 461-467.

Lujan, et al., "Tracking the mechanisms of deep brain stimulation for neuropsychiatric disorders," Front Biosci 13 (2008), pp. 5892-5904.

Lujan, J.L. et al., "Automated 3-Dimensional Brain Atlas Fitting to Microelectrode Recordings from Deep Brain Stimulation Surgeries," Stereotact. Fund!. Neurosurg. 87(2009), pp. 229-240.

Machado. et al., "Functional topography of the ventral striatum and anterior limb of the internal capsule determined by electrical stimulation of awake patients," Clin Neurophysiol 120 (11) (2009), pp. 1941-1948.

Malone, et al., "Deep brain stimulation of the ventral capsule/ventral striatum for treatment-resistant depression," Biol Psychiatry 65 (4) (2009), pp. 267-275.

VISUALIZATION OF RELEVANT STIMULATION LEADWIRE ELECTRODES RELATIVE TO SELECTED STIMULATION INFORMATION

CROSS-REFERENCE TO RELATED APPLICATIONS

The present application claims the benefit of U.S. Prov. Pat. App. Ser. No. 61/793,773 ("the '773 application"), filed Mar. 15, 2013.

The present application is also a continuation-in-part of U.S. patent application Ser. No. 13/481,524 ("the '524 application"), filed May 25, 2012, which claims the benefit of 61/491,092 ("the '092 application"), filed May 27, 2011.

The present application is also a continuation-in-part of U.S. patent application Ser. No. 13/481,497 ("the '497 application"), filed May 25, 2012, which claims the benefit of the '092 application.

The present application is also a continuation-in-part of each of U.S. patent application Ser. No. 14/011,817 ("the '817 application"), Ser. No. 14/011,836 ("the '836 application"), and Ser. No. 14/011,870 ("the '870 application"), each of which was filed Aug. 28, 2013 and claims the benefit of each of U.S. Prov. Pat. App. Ser. No. 61/693,866 ("the '866 application"), filed Aug. 28, 2012, 61/699,115 ("the '115 application"), filed Sep. 10, 2012, 61/699,135 ("the '135 application"), filed Sep. 10, 2012, and 61/753,232 ("the '232 application"), filed Jan. 16, 2013.

The contents of all of the '773, '524, '092, '497, '817, '836, '870, '866, '115, '135, and '232 applications are incorporated by reference herein in their entireties.

FIELD OF THE INVENTION

The present invention relates to a system and method for generating and outputting therapeutic stimulation-related information in relation to electrodes of an implanted leadwire usable for electrically stimulating an anatomical region. Such output can be provided on a patient-specific basis and/or on an implant-position basis. The leadwire can be, e.g., of a Deep Brain Stimulation (DBS) device or a Spinal Cord Stimulation (SCS) device. Features of the present invention can aid the selection of electrical stimulation parameters for performing anatomic stimulation using the leadwire.

BACKGROUND

Stimulation of anatomical regions of a patient is a clinical technique for the treatment of disorders. Such stimulation can include deep brain stimulation (DBS), spinal cord stimulation (SCS), Occipital NS therapy, Trigemenal NS therapy, Vagus NS therapy, peripheral field stimulation therapy, sacral root stimulation therapy, or other such therapies. For example, DBS can include stimulation of the thalamus or basal ganglia and may be used to treat disorders such as essential tremor, Parkinson's disease (PD), and other physiological disorders, including psychiatric disorders. DBS can also be useful for traumatic brain injury and stroke. Pilot studies have also begun to examine the utility of DBS for treating dystonia, epilepsy, and obsessive-compulsive disorder.

However, understanding of the therapeutic mechanisms of action remains elusive. The stimulation parameters, electrode geometries, or electrode locations that are best suited for existing or future uses of DBS also are unclear.

For conducting a therapeutic stimulation, a neurosurgeon can select a target region within the patient anatomy, e.g., within the brain for DBS, an entry point, e.g., on the patient's skull, and a desired trajectory between the entry point and the target region. The entry point and trajectory are typically carefully selected to avoid intersecting or otherwise damaging certain nearby critical structures or vasculature. A stimulation electrode leadwire used to provide the stimulation to the relevant anatomical region is inserted along the trajectory from the entry point toward the target region. The stimulation electrode leadwire typically includes multiple closely-spaced electrically independent stimulation electrode contacts.

The target anatomical region can include tissue that exhibit high electrical conductivity. For a given stimulation parameter setting, a respective subset of the fibers are responsively activated. A stimulation parameter can include a current amplitude or voltage amplitude, which can be the same for all of the electrodes of the leadwire, or which can vary between different electrodes of the leadwire. The applied amplitude setting results in a corresponding current in the surrounding fibers, and therefore a corresponding voltage distribution in the surrounding tissue. The complexity of the inhomogeneous and anisotropic fibers makes it difficult to predict the particular volume of tissue influenced by the applied stimulation.

A treating physician typically would like to tailor the stimulation parameters (such as which one or more of the stimulating electrode contacts to use, the stimulation pulse amplitude, e.g., current or voltage depending on the stimulator being used, the stimulation pulse width, and/or the stimulation frequency) for a particular patient to improve the effectiveness of the therapy. Parameter selections for the stimulation can be achieved via tedious and variable trial-and-error, without visual aids of the electrode location in the tissue medium or computational models of the volume of tissue influenced by the stimulation. Such a method of parameter selection is difficult and time-consuming and, therefore, expensive. Moreover, it may not necessarily result in the best possible therapy.

Systems have been proposed that provide an interface that facilitates parameter selections. See, for example, U.S. patent application Ser. No. 12/454,330, filed May 15, 2009 ("the '330 application"), U.S. patent application Ser. No. 12/454,312, filed May 15, 2009 ("the '312 application"), U.S. patent application Ser. No. 12/454,340, filed May 15, 2009 ("the '340 application"), U.S. patent application Ser. No. 12/454,343, filed May 15, 2009 ("the '343 application"), and U.S. patent application Ser. No. 12/454,314, filed May 15, 2009 ("the '314 application"), the content of each of which is hereby incorporated herein by reference in its entirety.

The leadwire can include cylindrically symmetrical electrodes, which, when operational, produce approximately the same electric values in all positions at a similar distance from the electrode in any plane that cuts through the electrode. Alternatively, the leadwire can include directional electrodes that produce different electrical values depending on the direction from the electrode. For example, the leadwire can include multiple separately controllable electrodes arranged cylindrically about the leadwire at each of a plurality of levels of the leadwire. Each electrode may be set as an anode or cathode in a bipolar configuration or as a cathode, with, for example, the stimulator casing being used as ground, in a monopolar arrangement.

When programming a leadwire for tissue stimulation, e.g., DBS, the clinical standard of care is often to perform a monopolar review (MPR) upon activation of the leadwire in order to determine the efficacy and side-effect thresholds for all electrodes on the leadwire, on an electrode-by-electrode basis. Monopolar review, rather than bipolar review, is performed because monopolar stimulation often requires a lower stimulation intensity than bipolar stimulation to achieve the same clinical benefit. The MPR can inform the selection of a first clinical program (parameters for stimulation) for treating a patient.

Example systems for programming a leadwire for tissue stimulation display a graphical representation of an area within which it is estimated that there is or could be tissue activation, referred to herein as a volume of activation (VOA), that results from input stimulation parameters. For example, the VOA can be calculated as a region outside of which stimulation is estimated to be unlikely. The VOA can be displayed relative to an image or model of a portion of the patient's anatomy.

Generation of the VOA may be based on Neural Element Models such as a model of fibers, e.g., axons, and a voltage distribution about the leadwire and on detailed processing thereof. Performing such processing to provide a VOA preview in real-time response to a clinician's input of parameters is not practical because of the significant required processing time. Therefore, conventional systems pre-process various stimulation parameter settings to determine which axons are activated by the respective settings.

Those systems also provide interfaces via which to input selections of the stimulation parameters and notes concerning therapeutic and/or side effects of stimulations associated with graphically represented VOAs. The systems also allow user input of, or automatically determine, a target stimulation region, e.g., within or encompassing one or more defined anatomic structures, or allow user input of, or automatically determine, a target defined anatomic structure, which target region or structure is targeted for stimulation.

SUMMARY

Example embodiments of the present invention provide a system and method that generates a map including a representation of stimulation leadwire electrodes and graphical markings visually indicating most significant ones of the electrodes with respect to particular stimulation-related information. In an example embodiment, the stimulation-related information represents an anatomic structure, e.g., the sub-thalamic nucleus (STN), targeted for stimulation. In an alternative example embodiment, the stimulation-related information represents an anatomic region targeted for stimulation. In an alternative example embodiment, the stimulation-related information represents regions that, when stimulated, are estimated to result in therapeutic success to achieve a good clinical effect, and/or a gradient in degree of such success. In an alternative example embodiment, the stimulation-related information represents regions that, when stimulated, are estimated to result in an adverse side effect, and/or a gradient in degree of such adverse side effects. In an example embodiment, the system and method generates the map based on a combination of two or more of the above-indicated types of stimulation-related information.

In an example embodiment of the present invention, the map includes a marking visually indicating a range of most significant electrodes and a further marking indicating the single most significant one of the electrodes with respect to the relevant stimulation-related information.

In an example embodiment of the present invention, the respective degrees of significance of different ones of the electrodes with respect to the relevant stimulation-related information, determined for the purpose of generating the map, is based on the respective proximities of the electrodes to an anatomic region associated with the stimulation-related information. In an example embodiment, in an instance where the leadwire does not pass through the associated anatomic region, proximity is determined based on the length of a ray that is perpendicular to the longitudinal axis of the leadwire and extends from the electrode to the associated anatomic region.

In an example embodiment of the present invention, the marking(s) provided in the generated map are provided in a grid formed by a first axis representing the different electrodes and a second axis representing a range of values of a selected stimulation parameter, e.g., stimulation amplitude. In an example embodiment of the present invention, the system records data pertaining to stimulations associated with particular values of the selected stimulation parameter using particular ones of the electrodes. Such data can include, for example, a therapeutic effect and/or adverse side effect determined or indicated to have occurred or estimated to occur, e.g., using particular ones of the values of the selected stimulation parameter at particular ones of the electrodes. In the example embodiment, the system plots graphical markings corresponding to respective ones of such recorded data at the electrode/stimulation value pair for which the respective datum had been recorded. In an example embodiment, the marking(s) indicating which of the electrodes are significant with respect to the stimulation-significant anatomic region are provided within the grid that includes the markings representing the recorded data, thereby providing an indication of the relationship of those electrodes which are or can be assumed to be significant with respect to the stimulation-significant anatomic region to the recorded data.

For example, in an example embodiment, the grid includes plotted therein a graphical marking representing a recorded occurrence of an adverse side effect of a stimulation centered at one of the electrodes at a particular stimulation amplitude. The marking is placed in the grid at the location corresponding to the electrode at which the stimulation was centered and corresponding to the amplitude of the stimulation. The grid also includes therein a marking showing which one or more of the electrodes correspond to a target stimulation region or structure, which therefore provides a visual indication of which one or more electrodes are most likely best able to be used for stimulating the target region or structure and how stimulation using those one or more electrodes might cause an adverse side effect. Since the grid plots the adverse side effect markers according to stimulation amplitude, the markings can help the user determine the electrode at which to center stimulation and the amplitude settings to avoid. Similarly, if the grid instead plots the markings representing the adverse side effects against a different stimulation setting, the grid would give the user an idea of which values to use or avoid for such other stimulation setting.

Therefore, according to an example embodiment of the present invention, the system and method provides in a graphical user interface an input component with which the user can select the stimulation parameter to be represented in the grid. The user can switch between different parameter types and, based on the plots of the markings in the different grids corresponding to the different parameter types, tailor stimulation settings.

In an example embodiment, the number of markings representing the side effects in the grid depends on the number of side effects that have been recorded, the severity of the recorded side effects, and/or filter criteria by which to filter which side effects to display. For example, such filter criteria can include age, sex, and/or condition of the patient whose stimulation resulted in the recorded side effect; severity of the side effect; and/or number of instances of the side effect at the particular stimulation location and stimulation parameter value, etc.

In an example embodiment, the markings representing the side effects are displayed to indicate the severity or, and/or the number, of the recorded adverse side effects corresponding to the grid position. For example, a number or making size can be used to represent the number of recorded side effects, or a number or marking size can be used to represent the severity of the recorded side effects (e.g., an average of all recorded side effects corresponding to the grid location). Alternatively, for example, a size can be used to indicate severity and a number can be used to indicate the number of recorded side effects. For example, the number can be the marking, and its size can vary depending on severity. Other indicia can be used instead or in addition. For example, degrees of transparency or different colors can be used to represent different severities or numbers.

As noted above, the markings can represent adverse side effects or therapeutic effect, number and severity being indicated according to an example embodiment regardless of which is represented. In an example embodiment, makings can be included for both therapeutic effect and side effect. The markings can be differently output depending on whether they represent therapeutic effect or adverse side effect. For example, different colors and/or shapes can be used depending on whether a marking represents a therapeutic effect or a side effect.

In an example embodiment of the present invention, the effect markings are selectable, in response to which selection additional details are provided regarding the corresponding therapeutic effects and/or adverse side effects. For example, the '330, '312, '340, '343, and '314 applications describe notes entered by a user using a graphical user interface components. In an example embodiment, in response to selection of a marking in the grid, which marking represents a therapeutic or adverse side effect, the system outputs, e.g., displays in a graphical user interface, such a note previously input in association with the effect, or outputs a further interface component by which such a note is selectable for viewing.

In an example embodiment of the present invention, information on which basis the markings representing the therapeutic and/or side effects are based are obtained automatically using sensors and/or by user input, for example, as described in any of the '330, '312, '340, '343, '314, '866, and '135 applications.

In an example embodiment of the present invention, the markings visually indicating most significant ones of the electrodes with respect to particular stimulation-related information such as a target region, and/or the markings representing recorded information associated with stimulations centered at one or more of the electrodes at particular stimulation parameter settings, as described above, are displayed in a graphical user interface display including a plurality of tabs and are displayed in association with a first one of the plurality of tabs, where others of the tabs are selectable for display of other stimulation-related information. In an example embodiment of the present invention, one of the other tabs is selectable for display, in response to its selection, of volume of activation (VOA) information, for example, as described in the '330, '312, '340, '343, '314, '115, and '232 applications. For example, in an example embodiment, the other tab is selectable for display of a representation of the target region for which the first tab indicates the electrodes most likely to be relevant, the target region being displayed relative to a displayed representation of anatomic regions of a patient. Such a representation of the target region can be in a two-dimensional format or a three-dimensional format. In an alternative example embodiment, the other tab is selectable for display of a volume representing gradations in therapeutic and/or adverse side effects relative to anatomic regions of a patient. Such a representation can be in a two-dimensional format or a three-dimensional format. In an example embodiment, one of the other tabs is selectable for display of the target region relative to anatomic structures and another of the other tabs is selectable for display of the volume representing the described gradations. The user can accordingly quickly switch between a number of views, each providing different types of information concerning possible stimulations, and accordingly decide on which stimulation parameters to set for the leadwire electrodes to produce a stimulation of tissue in a patient.

An example embodiment of the present invention is directed to one or more processors, which can be implemented using any conventional processing circuit and device or combination thereof, e.g., a Central Processing Unit (CPU) of a Personal Computer (PC) or other workstation processor, to execute code provided, e.g., on a hardware computer-readable medium including any conventional memory device, to perform any of the methods described herein, alone or in combination, and to generate any of the user interface displays described herein, alone or in combination. The one or more processors can be embodied in a server or user terminal or combination thereof. The user terminal can be embodied, for example, as a desktop, laptop, hand-held device, Personal Digital Assistant (PDA), television set-top Internet appliance, mobile telephone, smart phone, etc., or as a combination of one or more thereof. Specifically, the terminal can be embodied as a clinician programmer terminal, e.g., as referred to in the '330, '312, '340, '343, and '314 applications. Additionally, some of the described methods can be performed by a processor on one device or terminal and using a first memory, while other methods can be performed by a processor on another device and using, for example, a different memory.

The memory device can include any conventional permanent and/or temporary memory circuits or combination thereof, a non-exhaustive list of which includes Random Access Memory (RAM), Read Only Memory (ROM), Compact Disks (CD), Digital Versatile Disk (DVD), and magnetic tape.

An example embodiment of the present invention is directed to one or more hardware computer-readable media, e.g., as described above, on which are stored instructions executable by a processor to perform the methods and/or provide the user interface features described herein.

An example embodiment of the present invention is directed to a method, e.g., of a hardware component or machine, of transmitting instructions executable by a processor to perform the methods and/or provide the user interface features described herein.

BRIEF DESCRIPTION OF THE DRAWINGS

In the drawings, which are not necessarily drawn to scale, like numerals may describe similar components in different views. The drawings illustrate generally, by way of example, but not by way of limitation, various embodiments discussed in the present document.

DETAILED DESCRIPTION

Figure 1:
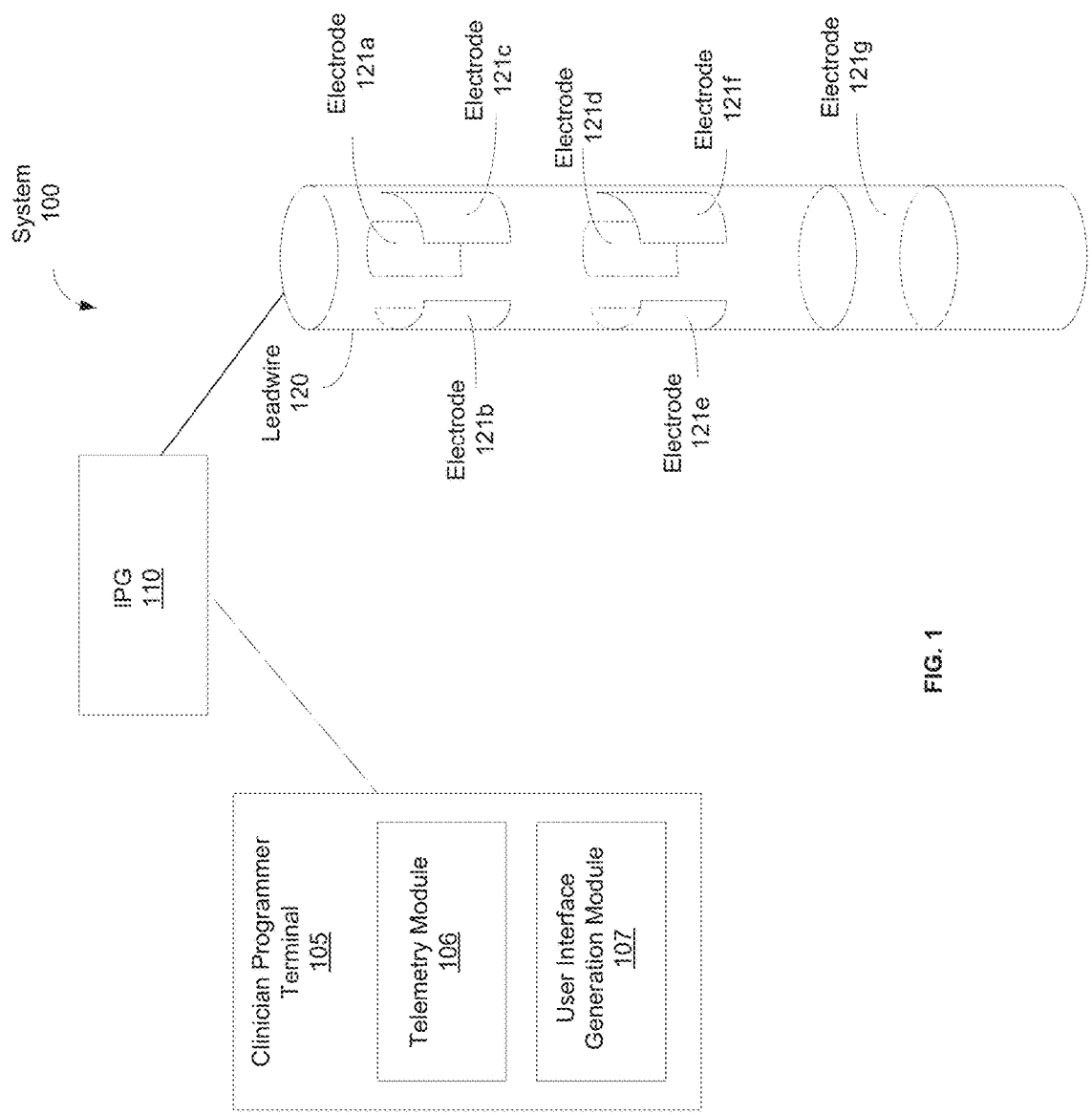
FIG. 1 shows an example stimulation and programming system according to an example embodiment of the present invention.

FIG. 1 shows an example system according to an example embodiment of the present invention. In an example embodiment, a system 100 includes a clinician programmer terminal 105 that includes a telemetry module 106 and a user interface generation module 107. The telemetry module is in communication with an implanted pulse generator (IPG) 110. The user interface generation module 107 includes software executable by a processor for generating graphical user interface displays. In an example embodiment, interaction with one or more graphical user interface displays and/or a hardware input device is usable for input of one or more stimulation parameter settings in accordance with which the telemetry module 106 outputs instructions to the IPG 110, the IPG 110 accordingly controlling a leadwire 120 to activate one or more electrodes 121a-121g to produce electric pulses at specified amplitudes. For example, the leadwire 120 is implanted in a patient, e.g., in the patient's brain, and the electric pulses are intended to activate anatomic fibers to produce a therapeutic effect, e.g., as described in further detail in the '330, '312, '340, '343, and '314 applications. The electrodes 121a-121g can include one or more directional electrodes which can be controlled to direct stimulation in a particular radial direction from the central longitudinal axis of the leadwire 120 and/or can include one or more cylindrical electrodes that produce essentially the same stimulation in all directions rotationally about the cylindrically symmetrical stimulation about the central longitudinal axis of the leadwire 120.

Figure 2:
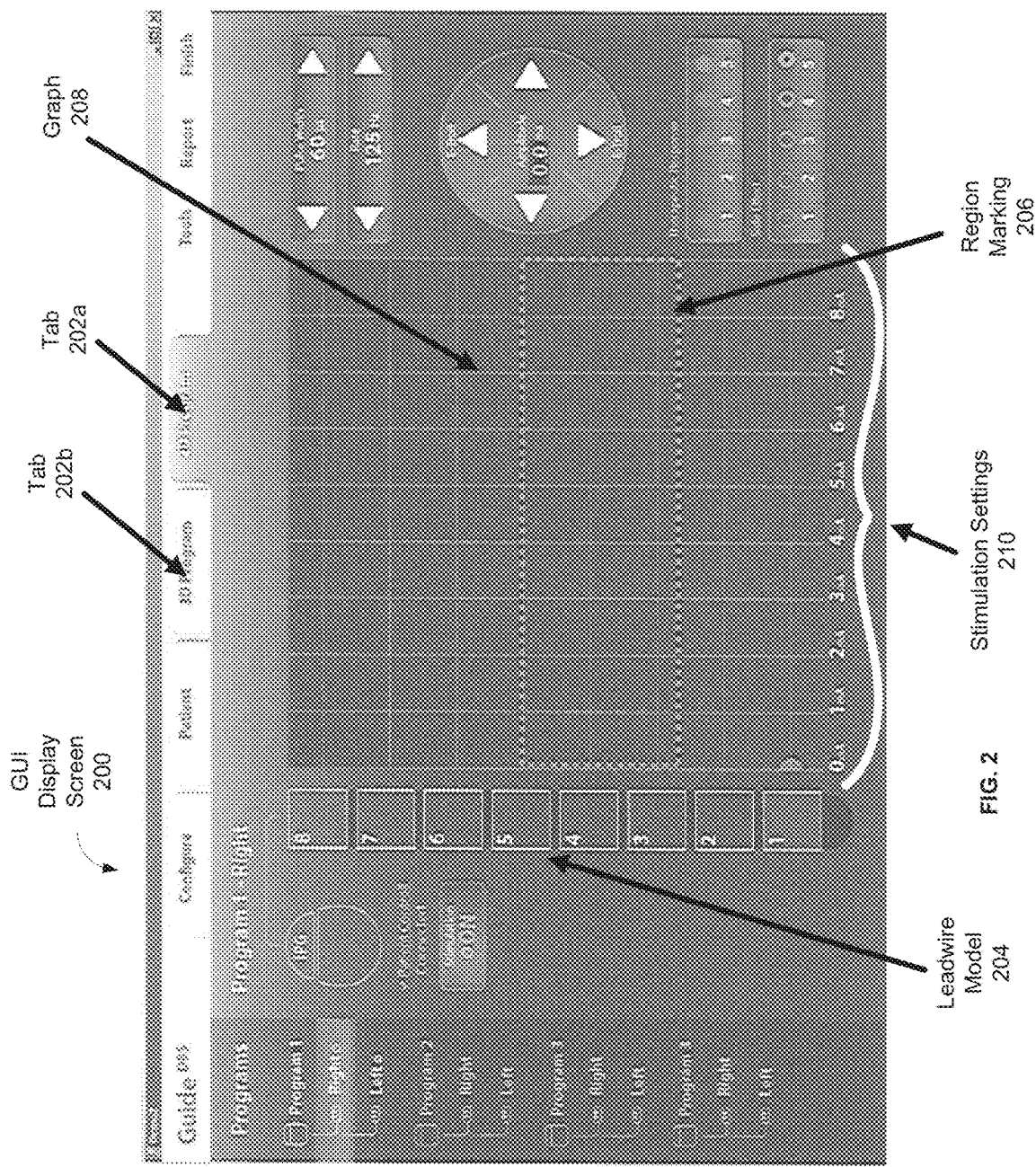
FIG. 2 shows an example display screen generable by the system, including a marking showing one or more electrodes that are proximal to a stimulation significant region, according to an example embodiment of the present invention.

FIG. 2 shows an example of a user interactive graphical user interface display screen 200, according to an example embodiment of the present invention. The example display screen 200 includes a leadwire model 204 that represents a leadwire, e.g., the implanted leadwire 120. The leadwire model 204 includes representations of each of a plurality of electrodes of the leadwire. In the example display screen 200, each of eight electrodes arranged at eight different locations along the longitudinal axis of the leadwire 120 are represented by respectively numbered vertically stacked regions of the leadwire model 204. Although shown vertically stacked, in an alternative example embodiment, the leadwire model 204 can be horizontally orientated, in which the respectively number regions would be arranged horizontally beside one another.

The example display screen 200 further includes a region marking 206 that vertically (since the leadwire model 204 is vertically arranged in the illustrated embodiment) spans those of the electrode representing regions that correspond to electrodes determined by the processor, e.g., by a currently performed calculation or by look-up of previously recorded data, to most closely correspond to an anatomic region or structure of significance with respect to particular stimulation-related information. For example, in an example embodiment, the anatomic region or structure of significance is that which is targeted for stimulation, e.g., as manually defined by user input or as automatically determined by the processor.

Figure 3:
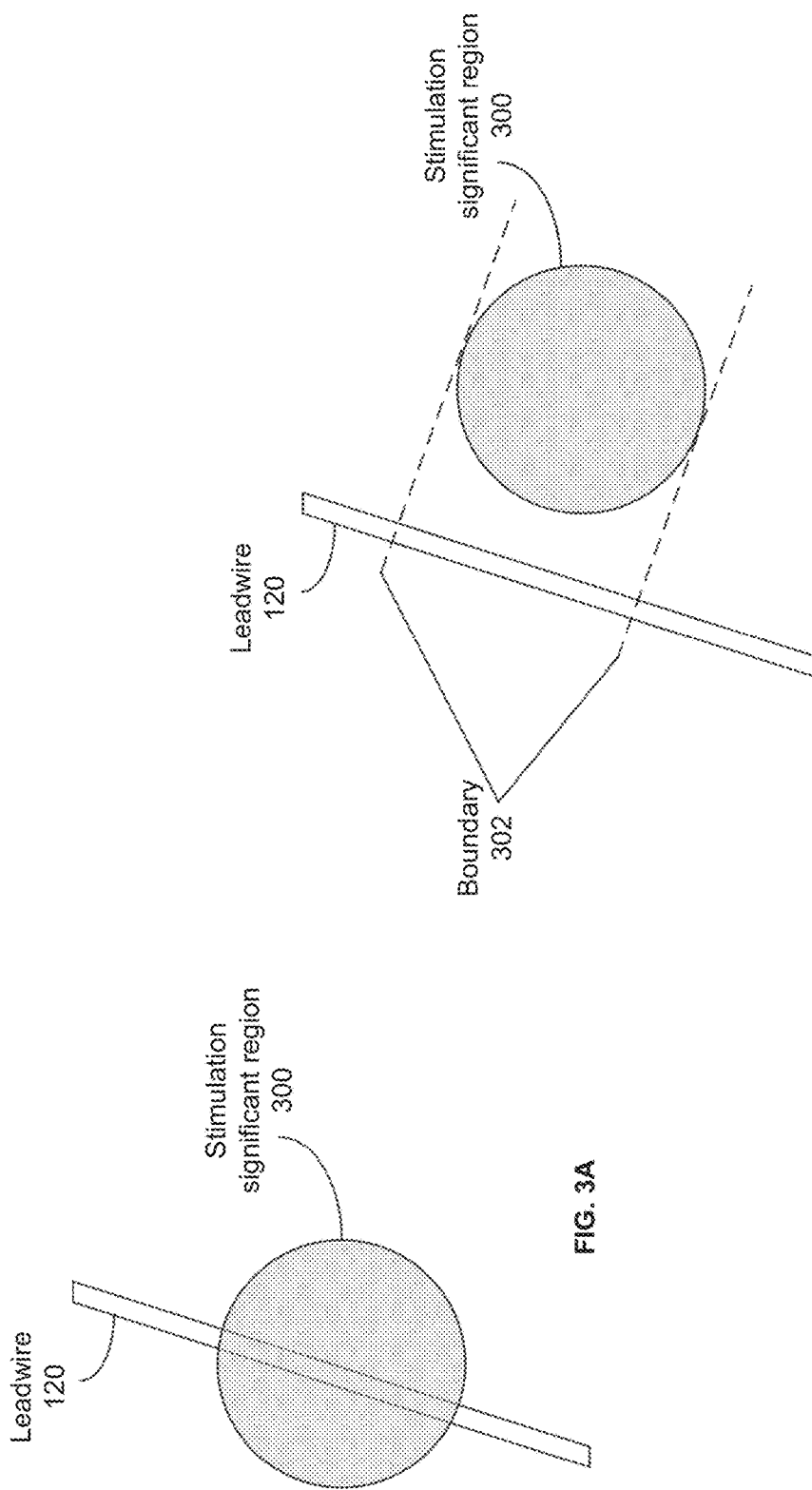
FIG. 3A illustrates the passing of a leadwire through a stimulation significant region on which basis display screens are generable according to example embodiments of the present invention.
FIG. 3B illustrates a region considered to be significant, according to an example embodiment of the present invention, for generating the described display screens, in an instance where the leadwire does not pass through the stimulation significant region.

In an example embodiment, in an instance where at least one of the electrodes of the leadwire 120 passes through the region or structure of significance, an electrode is deemed by the processor to be sufficiently closely related to the region or structure of significance to be indicated as such conditional upon that the respective electrode is one of the electrodes that pass through the region or structure of significance. For example, FIG. 3A shows an example stimulation significant region 300 through which the leadwire 120 passes, an example instance in which region marking 206 would identify only those electrodes that are at least partially within the stimulation significant region 300. According to an alternative example embodiment, at least where at least one of the electrodes is completely within the stimulation significant region 300, the region marking 206 would identify only those electrodes that are completely within the stimulation significant region 300.

However, it can occur that the stimulation significant region 300 is offset from the leadwire 120 as shown in FIG. 3B, where the leadwire 120 does not pass through the stimulation significant region 300, and therefore none of the electrodes 121a-121g are contained within the stimulation significant region 300. According to an example embodiment of the present invention, in such an instance, the processor deems an electrode to be sufficiently closely related to the region or structure of significance to be indicated as such by the region marking 206 conditional upon that the electrode is within a boundary 302 whose boundary lines are drawn perpendicular to the central longitudinal axis of the leadwire 120 and define upper and lower limits of the stimulation significant region 300 with respect to the orientation of the boundary 302.

The region marking 206 shown in FIG. 2 is a box whose upper and lower limits are drawn such that all of the electrodes deemed to be sufficiently closely related to the stimulation significant region 300 are beside the box. In an alternative example embodiment, the region marking 206 is formed of two horizontal lines (where the leadwire model 204 has a vertical orientation) drawn such that all of the electrodes deemed to be sufficiently closely related to the stimulation significant region 300 are beside the region that is between the two horizontal lines. In an alternative example embodiment, the region marking 206 is a single vertical line (e.g., the left vertical line of the box shown in FIG. 2) that extends beside all of the electrodes deemed to be sufficiently closely related to the stimulation significant region 300.

As noted above, according to example embodiments, whether an electrode is deemed sufficiently closely related to the stimulation significant region 300 is based on proximity of the electrode to the stimulation significant region 300 (in that it either passes through the region in the case shown in FIG. 3A or is within the boundary 302 in the case shown in FIG. 3B). This information is important for a user because greater proximity of a first electrode to the stimulation significant region 300 than a second electrode suggests that the first electrode is likely a better candidate than the second electrode for contributing to the stimulation of the stimulation significant region 300. The user may accordingly test settings with activation of the first electrode, e.g., at greater amplitude than that at which the second electrode is set, for the stimulation.

However, proximity to the stimulation significant region 300 is not necessarily all that is considered to determine which electrodes to activate and the amplitudes at which the electrodes are to be set. According to an example embodiment, the region marking 206 is therefore presented as a two dimensional element, e.g., a box as shown in FIG. 2 or two horizontal lines bounding a region, such that the element covers a region in which other information is presented which can further factor into the user's decision for setting the stimulation parameters of the leadwire 120.

For example, in FIG. 2, the leadwire model 204 and its numbered regions are arranged as values of the ordinate of a graph 208, and values for a particular stimulation parameter are arranged as the abscissa values of the graph 208. Specifically, FIG. 2 shown amplitude values as stimulation settings 210 for the abscissa of the graph 208. In alternative embodiments, values of other stimulation parameters can be used as the abscissa values. In alternative example embodiment, the processor provides a user interface via which a user can select one of a plurality of stimulation parameters to use for the abscissa. As noted above, in an alternative example embodiment, the leadwire model 204 can be horizontally arranged, in which case the electrodes would form the abscissa values and the values of the used parameter would form the ordinate values.

According to these example embodiments in which values of a stimulation parameter are arranged in a graph against the leadwire model 204, although not shown in FIG. 2, data corresponding to a stimulation associated with a particular electrode (or region to which the particular electrode is proximal) and associated with a particular one of the values of the represented stimulation parameter is plotted in the graph at the corresponding values (corresponding electrode and corresponding parameter value). For example, if an adverse side effect had been recorded to have occurred at a stimulation centered about electrode 3 at an amplitude of 3 mA, in an example embodiment, a node is plotted in the graph at the intersection of electrode 3 and 3 mA. By identifying which electrodes are most likely relevant for stimulating the target stimulation region, while also identifying which combinations of electrodes and stimulation amplitudes previously produced an adverse side effect, the user can identify which electrodes and amplitude settings are best candidates for stimulating the target region without producing an adverse side effect.

According to an example embodiment, the recorded information is information previously recorded for the current patient for whom the target stimulation region has been identified and for whom stimulation parameters are being selected based on the output data. According to an alternative example embodiment, information recorded for other patients is also represented.

Different types of information can be recorded in association with the electrode parameter value combinations. For example, particularly good therapeutic effects can be recorded. According to an example embodiment of the present invention, more than one data category is representable in the graph. For example, where both adverse side effects information and therapeutic effect information is recorded, the processor outputs graph nodes for both adverse side effects and therapeutic effects records. For example, different graphical markings can be used depending on the type of information, e.g., adverse side effect versus therapeutic effect, being represented. Additionally, according to an example embodiment, the graphical markings representing the graph nodes are differently presented depending on variations in degree. For example, as described with respect to FIG. 6 of the '135 application, aside from inputting occurrences of an adverse side effect and/or therapeutic effects, degrees of such effects can also be input and recorded. Accordingly, the way in which a graph node representing, for example, an adverse side effect is displayed depends on the indicated severity of the adverse side effect. Similarly, the way in which a graph node representing, for example, a therapeutic effect is displayed depends on the indicated degree of therapeutic effect. It is possible for an adverse side effect or therapeutic effect to be recorded without an indication of degree of such effect. In an example embodiment, were no degree is indicated, the node is output in a manner specifically for an instance in which degree has not been indicated. Alternatively, where no degree is specified, a default degree is assigned to the data.

For example, in an example embodiment, a green node is used to represent a therapeutic effect and a red node is used to represent an adverse side effect. Also, for example, the greater degree of the effect, the larger the displayed node. Alternatively, for example, different transparencies are used depending on degree. For example, the greater the degree of the adverse side effect, the more opaque the red node. Alternatively, a scale of color is used, where the greater the degree of the effect, the deeper the red or the green used for the display of the corresponding node.

Figure 4:
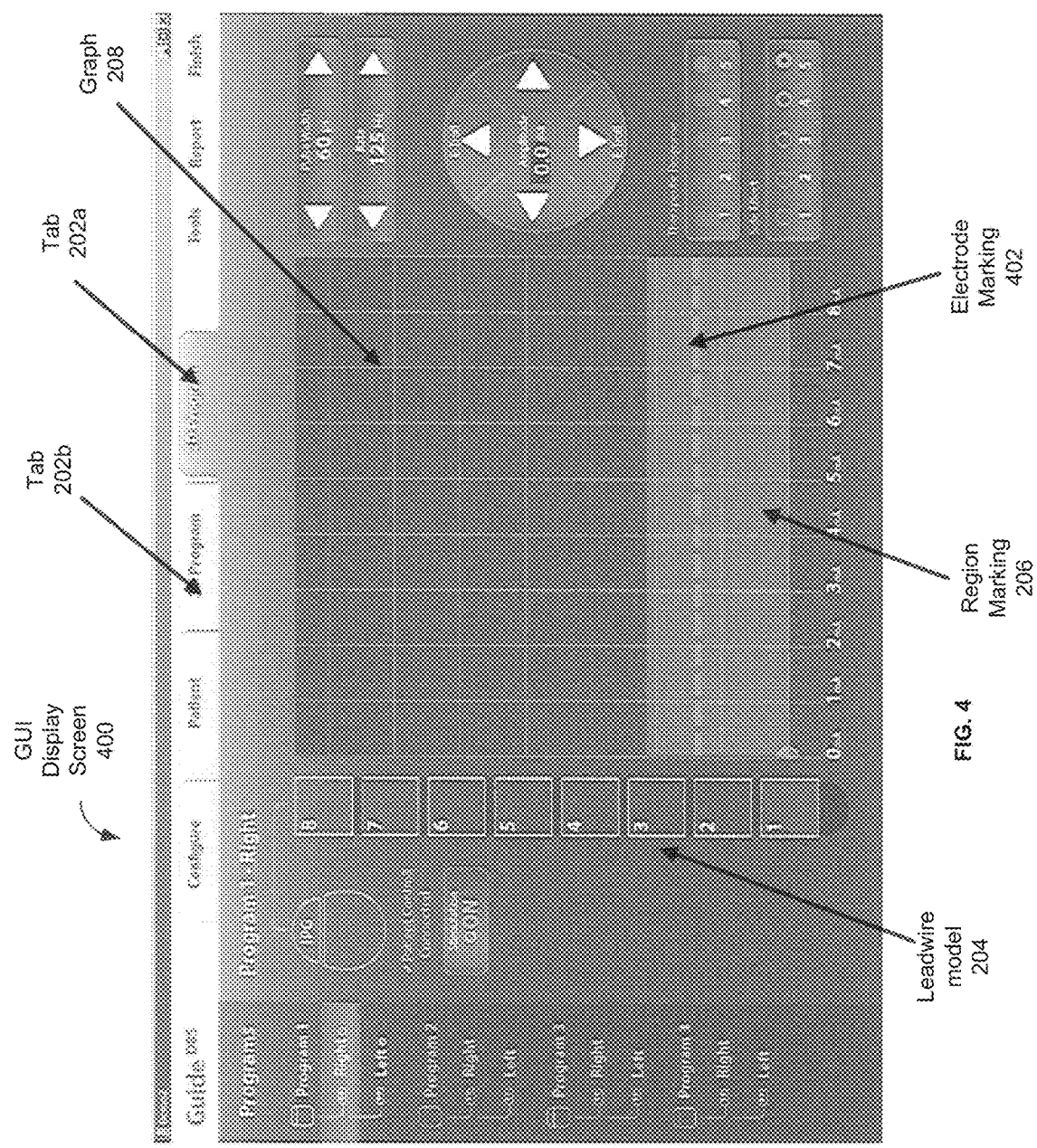
FIG. 4 shows an example display screen including a marking identifying the locationally relevant electrodes and an additional marking identifying the electrode corresponding to a sub-area within the stimulation significant region, according to an example embodiment of the present invention.

According to an example embodiment of the present invention, instead of or in addition to graphically demarcating all electrodes that are within or are proximate to the stimulation significant region 300, the system graphically indicates the single electrode that intersects or is closest to (with respect to a region drawn perpendicularly to the central longitudinal axis of the leadwire 120 and that bounds upper and lower boundaries of the stimulation significant region 300) a significant sub-area within the stimulation significant region 300, e.g., the center or centroid of the stimulation significant region 300 or a region that has been user-indicated to have particular significance. For example, FIG. 4 shows a GUI display screen 400, similar to GUI display screen 200 shown in FIG. 2, but display screen 400 further includes an electrode marking 402 corresponding to a single electrode level corresponding to the significant sub-area within the stimulation significant region 300.

In an example embodiment of the present invention, instead of providing the region marking 206 and/or electrode marking 402 such that they correspond to particular electrodes, they are provided to correspond to particular locations or levels of the leadwire with respect to its longitudinal axis. For example, the region marking 206 in FIG. 2 does not correspond to the entirety of electrodes 3 to 5, but rather includes the entirety of electrode 4, most of electrode 3, and approximately half of electrode 5, for example, because only parts of electrodes 3 and 5 are within stimulation significant region 300 or within boundary 302. Similarly, in FIG. 4, electrode marking 402 is at the very top of electrode 2. Further, in an example embodiment, if the relevant upper and lower limits of the stimulation significant region 300 and/or significant sub-area within the stimulation significant region 300 corresponds to a level of the leadwire 120 at which there is no electrode, e.g., between electrodes, the upper and lower edges of the region marking 206 and/or the electrode marking 402 is placed at the relevant leadwire level at which none of the electrodes are represented, e.g., between two electrode representations. It is noted that settings of multiple electrodes can be set to center a stimulation between electrodes, such a center location being a virtual electrode location as described in the '135 application. Accordingly, for example, where the electrode marking 402 is positioned between two electrode representations, a user might therefore consider setting stimulation parameter settings for those two electrodes to center a stimulation at the virtual electrode position between them, which corresponds to the leadwire level at which the electrode marking 402 is drawn.

Although display of a leadwire model 204 with a marking showing those electrodes that are significant based on proximity to a stimulation significant region 300, such as a selected target stimulation region, in a graph that plots information corresponding to the electrodes (or virtual electrodes) at particular values of a selected stimulation parameter, provides a quick reference for a user to visually ascertain those electrodes for which settings can quickly and easily be ascertained, e.g., by trial and error, for producing a stimulation that will likely stimulate the target region, it is also of benefit to provide other interface displays with more detailed and/or other types of information relevant for selecting stimulation parameters, e.g., displays as described in the '330, '312, '340, '343, '314, and/or '232 applications. For example, such other displays can include one or more stimulation significant three-dimensional volumes. Additionally, it is useful for the user to be able to separately view such detailed graphical representations and the core electrode-location information described with respect to FIGS. 2 and 4 to observe how they relate to each other.

Therefore, according to an example embodiment of the present invention, the system outputs a user interface with which a user can quickly switch between two (or more views) including the different graphical information. For example, FIGS. 2 and 4 show tabs 202a and 202b, where the above-described core electrode-location information is shown when the tab 202a is selected. The user can select the tab 202b to view other types of information. For example, in example embodiment, when tab 202b is selected, the system displays one or more of the graphical displays described with respect to the figures of the '232 application, e.g., including detailed three-dimensional side effect and/or therapeutic effect regions and/or gradients.

In an example embodiment of the present invention, instead of using a target stimulation region as the stimulation significant region 300, a region associated with adverse side effect and/or therapeutic effect is used as the stimulation significant region. For example, within an anatomical region, in an example embodiment of the present invention, voxels are assigned respective scores, e.g., based on the number of stimulation regions associated with therapeutic effect in which the respective voxels were included and the number of stimulation regions associated with adverse side effect in which the respective voxels were included. For example, a score threshold can be selected, and, in an example embodiment, the region marking 206 is based on a region in which all or a majority of voxels are assigned scores that meet the threshold.

In an example embodiment, the regions of adverse side effect are regions recorded to have been associated with at least a threshold level of adverse side effect. In an alternative example embodiment, the regions of adverse side effect are regions recorded to have been associated with at least a threshold level of adverse side effect without at least a threshold level of therapeutic effect. In an alternative example embodiment, as described above, the regions of adverse side effect are regions assigned a score associated with adverse side effect, where the score is based on recorded data of adverse side effect and therapeutic effect, where recorded adverse side effects negatively impact the score and recorded therapeutic effects positively impact the score.

In an example embodiment, recorded data concerning adverse side effects and/or therapeutic effects are associated with tissue regions that have been previously stimulated. Often, adverse side effects are recorded for stimulation regions in which there is one or more smaller stimulation regions that resulted from other stimulations, which other smaller stimulation regions have been associated with therapeutic effect.

Therefore, recorded adverse side effect regions can be separated by a therapeutic effect region. In an example embodiment, multiple region markings 206 are output, each corresponding to a respective stimulation significant region 300. For example, for a region associated with therapeutic effect that is bounded by regions associated with adverse side effects, resulting in two or more separate regions of adverse side effect, in an example embodiment, a respective region marking 206 is output for each of the separate regions of adverse side effect.

Figure 5:
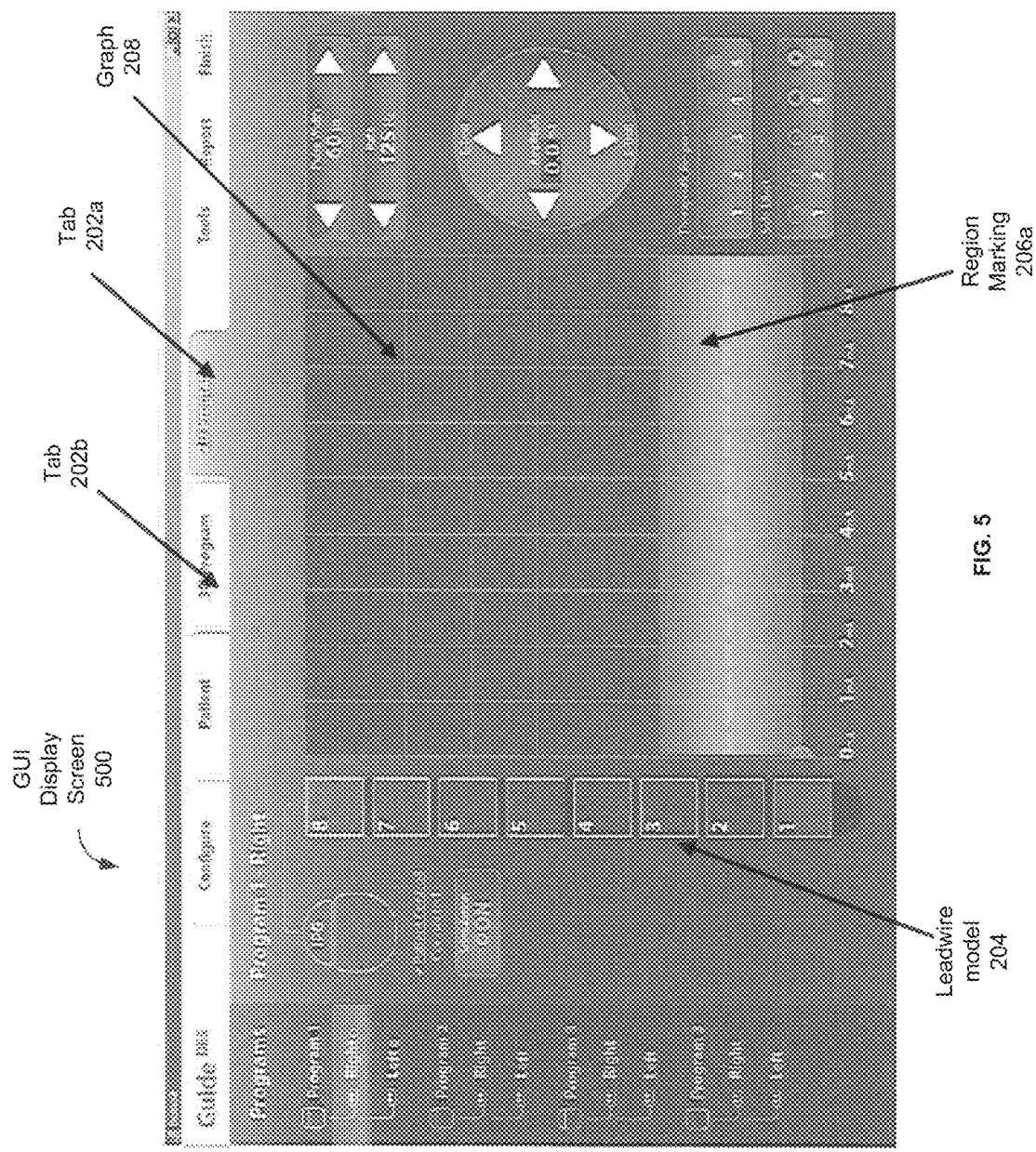
FIG. 5 shows an example display screen in which variations in therapeutic and/or side effect scores are graphically identified by variations in opacity/transparency, according to an example embodiment of the present invention.

According to an example embodiment of the present invention, as shown in FIG. 5, of the region whose voxels satisfy the score threshold, a gradient of the score is further graphically represented in the user interface display. For example, FIG. 5 shows a GUI display screen 500 including a region marking 206a showing the vertical position, relative to the leadwire 120, of the anatomic region whose scores satisfy the score threshold. The region marking 206a is a two-dimensional marking including a shaded area, in which transparency/opacity varies in accordance with changes in score.

For example, in an example embodiment, the better the score, the more opaque the part of the region marking 206a corresponding to the electrode location that is closest to that voxel.

An electrode might intersect both voxels of high score and low score. Therefore, according to an example embodiment, for an electrode that intersects voxels to which different scores are assigned, the opacity corresponding to the part of the region marking 206a that corresponds to the electrode is based on an average of the voxels' scores. Alternatively, another mathematical calculation can be used for selecting the opacity corresponding to the electrode (or leadwire level).

Similarly, where the leadwire does not intersect the region whose voxel scores satisfy the score threshold, an electrode might be close to both voxels of high score and low score. According to an example embodiment, in such a case, the processor performs a mathematical function whose input are the scores of all voxels within a region formed by planes drawn perpendicularly to the central longitudinal axis of the leadwire 120 and including the electrode, but assigns different weights to the voxel scores depending on proximity of the voxel to the electrode, where the closer the voxel is to the electrode, the greater its score is weighted.

According to an alternative example embodiment of the present invention, if an electrode intersects more than one voxel or, where the leadwire does not intersect the relevant region and therefore non-intersecting voxels are considered, the opacity/transparency is selected based on the highest scored voxel corresponding to the electrode (or leadwire level).

An example embodiment has been described above in which a region marking 206 corresponds to a target stimulation region, and an example embodiment has been described above in which a region marking 206a corresponds to a therapeutic effect region. According to an alternative example embodiment a region marking 206a is provided based on a combination of such information. For example, a target stimulation region is used as the boundary of the region marking 206a and variations in opacity/transparency within the region marking 206a are based on variations of voxel score within the target stimulation region. (It is noted that score threshold can itself be a factor for selecting the target stimulation region)

In example embodiments of the present invention more than one region marking 206 or 206a is displayed, e.g., where more than one region is targeted for stimulation or where more than one region of voxels satisfies the score threshold.

Referring to FIG. 5, aside from variations of opacity/transparency vertically within the region marking 206a, in an example embodiment, opacity/transparency is also varied horizontally (not shown) within the region marking 206a depending on differences in voxel score depending on a selected parameter setting, e.g., amplitude, to the values of which the abscissa of the graph 208 corresponds. For example, in an example embodiment, the opacity of the region marking 206a at a part of the graph 208 that corresponds to electrode 2 and 6 mA is based on scores of voxels corresponding to electrode 2 as described above, but limited to stimulations at 6 mA.

Figure 6:
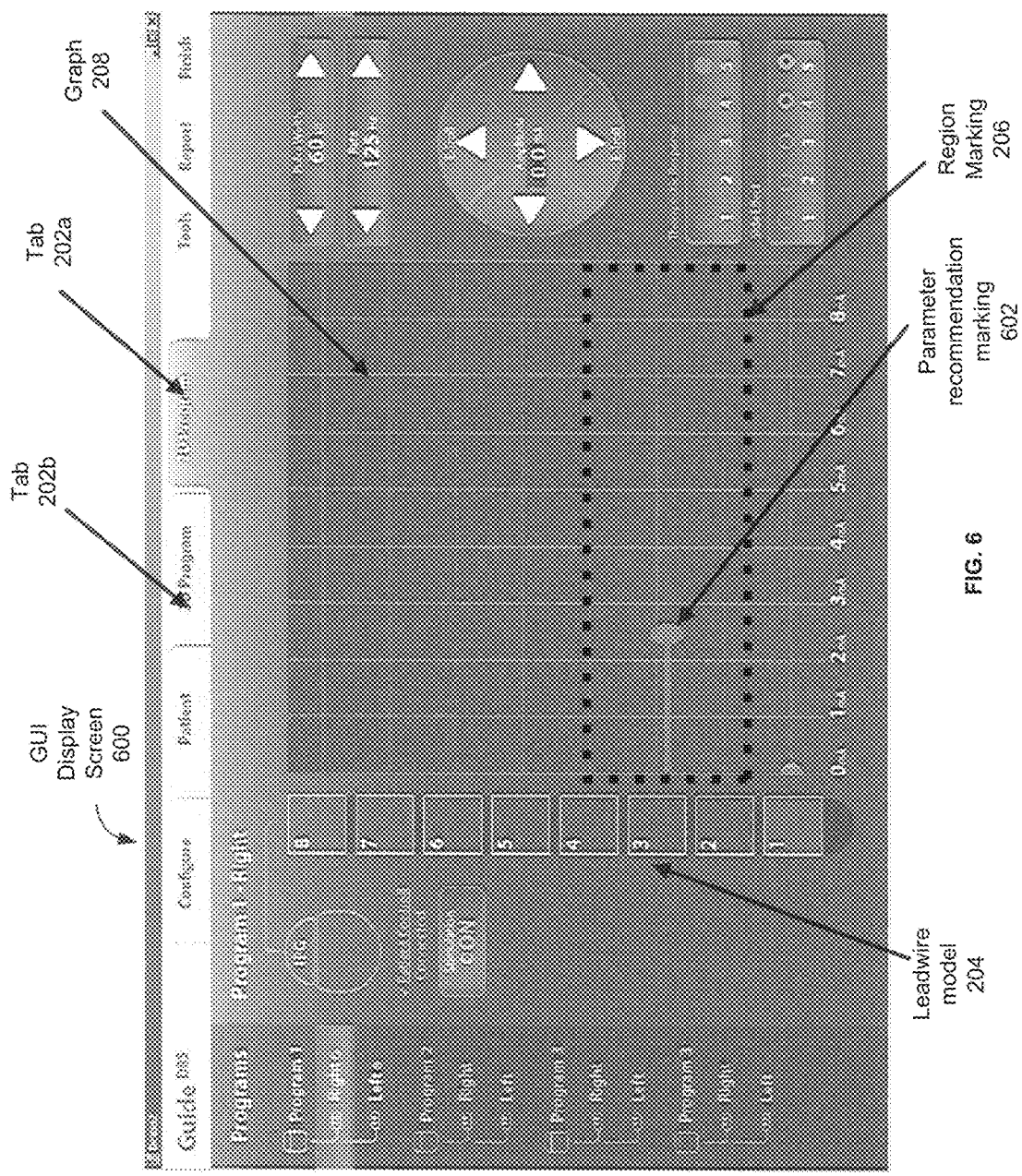
FIG. 6 shows an example display screen including a two-dimensional leadwire model and a parameter recommendation marking indicating a recommended value for a predetermined or selected stimulation parameter, according to an example embodiment of the present invention.

According to an example embodiment of the present invention, the system is configured to display a parameter recommendation marking 602 as shown in GUI display screen 600 of FIG. 6. The parameter recommendation marking 602 is displayed at a level corresponding to a part of stimulation significant region 300, e.g., a target stimulation region or structure, e.g., the center or centroid thereof, and is extended at that level until a point of the graph 208 that corresponds to a relevant value for a predetermined (or user-selected) stimulation parameter. For example, in FIG. 6, the abscissa of graph 208 corresponds to amplitude values, and the parameter recommendation marking 602 terminates at an amplitude value (between 2 and 3 mA) recommended for stimulation of the target region or structure. For example, according to an example embodiment, such a recommendation is obtained based on an algorithm that estimates an ideal amplitude setting for stimulating a region that best corresponds, e.g., based on, and, according to an example embodiment, considering a trade-off between, overlap and spill, to the target region or structure, e.g., as described in detail in U.S. Prov. Pat. App. Ser. No. 61/651, 282 ("the '282 application"), filed Aug. 28, 2012, the content of which is incorporated by reference herein in its entirety.

According to an alternative example embodiment, the parameter recommendation marking is displayed at a level corresponding to an electrode (or virtual electrode) recommended to be used.

According to an example embodiment of the present invention, and as shown in FIG. 6, the system displays both the parameter recommendation marking 602 and the region marking 206, e.g., as described with respect to any of FIGS. 2, 4, and 5 (the marking 206 described with respect to FIG. 2 being shown in FIG. 6). Additionally, as noted above, the region marking 206 or 206a, according to example embodiments of the present invention, show boundaries of an adverse side effect or therapeutic effect region. According to those embodiments, the parameter recommendation marking 602 shows the relationship between those electrodes corresponding to the adverse side effect or therapeutic effect region and the electrode corresponding to the target region or location or that is recommended to be used for stimulating the target region or location.

The above description is intended to be illustrative, and not restrictive. Those skilled in the art can appreciate from the foregoing description that the present invention can be implemented in a variety of forms, and that the various embodiments can be implemented alone or in combination. For example, the graph nodes corresponding to records of side effects and/or therapeutic effect described above with respect to FIG. 2 can also be output in any of the display screens described above with respect to FIGS. 4-6. Therefore, while the embodiments of the present invention have been described in connection with particular examples thereof, the true scope of the embodiments and/or methods of the present invention should not be so limited since other modifications will become apparent to the skilled practitioner upon a study of the drawings, specification, and following claims.

What is claimed is:

1. A computer-implemented method for graphically identifying candidate electrodes of a leadwire for stimulation of a patient anatomy, the method comprising:
    obtaining, by a computer processor, data corresponding to an anatomic region;
    identifying, by the processor, a spatial relationship between electrodes of the leadwire to the anatomic region;
    based on the identifying, selecting, by the processor, a subset of the electrodes of the leadwire;
    generating, by the processor and based on the obtained data and the selected subset, a graphical output arrangement that includes:
        a model of the leadwire including graphical representations of at least some of the electrodes; and
        a graphical selection marking identifying the selected subset of the electrodes; and
    displaying, by the processor, the graphical output arrangement on a display coupled to the processor.

2. The method of claim 1, wherein:
    the electrodes are arranged in succession along a length of the leadwire, between first and second ends of the leadwire; and
    the generation and arrangement of the graphical selection marking is performed to ensure that:
        a first end of the selection marking is arranged adjacent the electrode of the selected subset that, of the selected subset, is arranged closest to the first end of the leadwire; and a second end of the selection marking is arranged adjacent the electrode of the selected subset that, of the selected subset, is arranged closest to the second end of the leadwire.

3. The method of claim 2, wherein the graphical selection marking includes:
a first line arranged perpendicular to a longitudinal axis of the model of the leadwire and arranged adjacent to the electrode of the selected subset that, of the selected subset, is arranged closest to the first end of the leadwire; and
a second line arranged perpendicular to the longitudinal axis of the model of the leadwire and arranged adjacent to the electrode of the selected subset that, of the selected subset, is arranged closest to the second end of the leadwire.

4. The method of claim 2, wherein the graphical selection marking includes a line extending from the first end of the selection marking to the second end of the selection marking.

5. The method of claim 1, wherein the anatomic region is a region targeted for stimulation.

6. The method of claim 1, wherein the anatomic region is an anatomic structure targeted for stimulation.

7. The method of claim 1, wherein the anatomic region is defined by an association of the region with at least one adverse stimulation side effect.

8. The method of claim 1, wherein the anatomic region is defined by an association of the region with at least one therapeutic stimulation effect.

9. The method of claim 1, wherein the graphical output arrangement further includes a second graphical selection marking identifying one of the subset of the electrodes based on the spatial arrangement of the one of the subset of the electrodes with a sub-area of the anatomic region.

10. The method of claim 9, wherein the sub-area is a centroid of the anatomic region.

11. The method of claim 1, wherein, where the leadwire includes at least one electrode that passes through the anatomic region, only the at least one electrode is selected in the selecting step.

12. The method of claim 11, wherein the electrodes of the leadwire include at least one virtual electrode defined by activations of a combination of two or more of the electrodes.

13. The method of claim 1, wherein, where the leadwire does not include any electrodes that passes through the anatomic region, the selecting is performed such that each of the subset of the electrodes is at least partially included within a portion of the leadwire that is between a first line of projection that is perpendicular to a central longitudinal axis of the leadwire and extends to a first boundary of the anatomic region and a second line of projection that is perpendicular to the central longitudinal axis of the leadwire and extends to a second boundary of the anatomic region.

14. The method of claim 1, wherein the graphical output arrangement includes a graph, the model of the leadwire provides a first set of values of the graph, a set of values of a stimulation parameter are a second set of values of the graph, and the graphical output arrangement includes one or more nodes that each corresponds to a respective value pair including one of the first set of values and one of the second set of values.

15. The method of claim 14, wherein a node corresponds to a value of the first set of values if the node is associated with a stimulation conducted with an electrode to which the value of the first set of values corresponds.

16. The method of claim 15, wherein a node corresponds to a value of the second set of values if the node is associated with a stimulation conducted with the stimulation parameter being set to the value of the second set of values.

17. The method of claim 14, wherein a node corresponds to a value of the first set of values if the node is associated with a stimulation region centered at an electrode to which the value of the first set of values corresponds.

18. The method of claim 14, wherein the stimulation parameter is stimulation amplitude.

19. The method of claim 14, wherein each of at least one of the one or more nodes is selectable, in response to which selection, the processor is configured to display details of a record associated with the respective value pair of the respective node.

20. The method of claim 14, wherein each of at least one of the nodes represents one of a recorded adverse side effect of a stimulation conducted at the respective value pair and a recorded therapeutic effect of the stimulation conducted at the respective value pair.

21. The method of claim 14, wherein the graphical selection marking includes a first edge parallel to a first axis of the graph and a second edge parallel to a second edge of the graph.

22. The method of claim 21, wherein, where the one or more nodes includes at least one node whose respective value pair includes a value of the first set of values that corresponds to at least one of the subset of the electrodes, the at least one node is displayed within the graphical selection marking.

23. The method of claim 22, wherein the at least one node corresponds to the at least one of the subset of the electrodes if the respective value pair of the at least one node includes a value of the first set of values that corresponds to a location between two of the electrodes of the leadwire.

24. The method of claim 1, wherein the model is two-dimensional.

25. The method of claim 1, wherein:
the graphical output arrangement includes a first user-selectable tab and a second user-selectable tab, the model and the graphical selection marking being displayed in the display when the first user-selectable tab is active and the second user-selectable tab is inactive;
user-selection of the second user-selectable tab inactivates the first user-selectable tab and activates the second user-selectable tab; and
when the second user-selectable tab is active, a representation of at least one of the anatomic region and another anatomic region is displayed.

26. The method of claim 25, wherein the model is two-dimensional, and, when the second user-selectable tab is active, a three-dimensional version of the model is displayed.

27. The method of claim 25, wherein the graphical output arrangement is two-dimensional, and the representation of the at least one of the anatomic region and the other anatomic region displayed when the second user-selectable tab is active is three-dimensional.

28. The method of claim 25, wherein the representation of the other anatomic region is displayed, and the other anatomic region is defined by at least one of (a) at least one recorded adverse stimulation side effect and (b) at least one recorded therapeutic stimulation effect.

29. The method of claim 1, wherein the graphical selection marking is two-dimensional and includes an area in which a graphical characteristic of the graphical selection marking varies based on differences in scores assigned to different locations within the anatomic region.

30. The method of claim 29, wherein the variation of the graphical characteristic is in each of the two dimensions of the graphical selection marking, the variation in the first of the two dimensions being based on differences in score for different levels along a longitudinal axis of the leadwire, and the variation in the second of the two dimensions being based on differences in score for different settings of a stimulation parameter.

31. The method of claim 30, wherein the stimulation parameter is stimulation amplitude.

32. The method of claim 1, wherein the graphical output arrangement further includes a suggestion marker arranged adjacent one of the electrodes, and being of a length that identifies a suggested setting for a stimulation parameter.

33. The method of claim 32, wherein the stimulation parameter is stimulation amplitude.

* * * * *